(12) United States Patent
Curtiss, III

(10) Patent No.: US 6,872,547 B1
(45) Date of Patent: Mar. 29, 2005

(54) FUNCTIONAL BALANCED-LETHAL HOST-VECTOR SYSTEMS

(75) Inventor: Roy Curtiss, III, St. Louis, MO (US)

(73) Assignee: Washington University, St. Louis, MO (US)

(*) Notice: Subject to any disclaimer, the term of this patent is extended or adjusted under 35 U.S.C. 154(b) by 194 days.

(21) Appl. No.: 09/686,499

(22) Filed: Oct. 11, 2000

(51) Int. Cl.$^7$ .......................... C12P 21/06; C12N 1/12; C12N 1/20; A61K 39/108; A61K 39/112

(52) U.S. Cl. ................ 435/69.1; 435/252.3; 435/252.1; 435/320; 435/471; 424/257.1; 424/258.1

(58) Field of Search .......................... 435/69.1, 252.3, 435/320, 252.1, 471; 424/258.1, 257.1

(56) References Cited

U.S. PATENT DOCUMENTS

| | | |
|---|---|---|
| 4,190,495 A | 2/1980 | Curtiss, III |
| 4,424,065 A | 1/1984 | Langhoff et al. |
| 4,550,081 A | 10/1985 | Stocker |
| 4,888,170 A | 12/1989 | Curtiss, III |
| 5,006,335 A | 4/1991 | Gluck et al. |
| 5,278,744 A | 1/1994 | Geboers et al. |
| 5,294,441 A | 3/1994 | Curtiss, III |
| 5,387,744 A | 2/1995 | Curtiss, III et al. |
| 5,389,368 A | 2/1995 | Curtiss, III |
| 5,424,065 A | 6/1995 | Curtiss, III et al. |
| 5,468,485 A | 11/1995 | Curtiss, III |
| 5,527,529 A | 6/1996 | Dougan et al. |
| 5,643,771 A | 7/1997 | Stocker |
| 5,656,488 A | 8/1997 | Curtiss, III et al. |
| 5,672,345 A | 9/1997 | Curtiss, III |
| 5,840,483 A * | 11/1998 | Curtiss, III .................... 435/6 |
| 5,851,519 A | 12/1998 | Dougan et al. |
| 5,855,879 A | 1/1999 | Curtiss, III |
| 5,855,880 A | 1/1999 | Curtiss, III |
| 5,888,790 A | 3/1999 | Cahoon et al. |
| 5,980,907 A | 11/1999 | Dougan et al. |
| 6,004,815 A * | 12/1999 | Portnoy et al. ............. 435/454 |
| 6,024,961 A * | 2/2000 | Curtiss, III et al. ...... 424/200.1 |

FOREIGN PATENT DOCUMENTS

WO   WO96/34631   11/1996   .......... A61K/48/00

OTHER PUBLICATIONS

Nayak et al. "A live recombinant avirulant oral salmonella vacine expressing pneumocopccal surface protein A induces protective response against *Streptococcus pneumonaie*" Infection and Immunity vol. 66, No. 8, pp. 3744–3751, 1998.*

Nayak et al. "A live recombinant avirulant oral salmonella vacine expressing pneumocopccal surface protein A induces protective response against *Streptococcus pneumonaie*" Infection and Immunity vol. 66, No. 8, pp. 3744–3751, 1998.*

Patrice Courvalin, Sylvie Goussard, Catherine Grillot–Courvalin, "Gene Transfer From Bacteria To Mammalian Cells," *Life Sciences,* 1995; pp. 1207–1212, 318, C.R. Adad, Paris.

Carmen Buchriesser, Phillippe Glaser, Christoph Rusniok, Hafed Nedjari, Helene D'Hauteville, Frank Kunst, Phillippe Sansonetti, and Claude Parsot, "The Virulence Plasmid pWR100 and the Repertoire of Proteins Secreted by the Type III Secretion Apparatus of Schigella Flexneri," *Molecular Biology,* (2000) pp. 760–771, 38(4), Blackwell Science Ltd, Paris.

Amann and Brosius (1985) *ATG vectors' for regulated high–level expression of cloned genes in Escherichia coli*; Gene 40: pp. 183–190.

Buchanan et al. (1987) *Characterization of Antibody–Reactive Epitopes on the 65–Kilodalton Protein of Mycobacterium leprae*; Infection and Immunity vol. 55, No. 4, pp. 1000–1003.

Curtiss and Kelly (1987) *Salmonella typhimurium Deletion Mutants lacking Adenylate Cyclase and Cyclic AMP Receptor Protein Are Avirulent and Immunogenic*; Infection and Immunity vol. 55, No. 12, pp. 3035–3043.

Darji et al. (1997) *Oral Somatic Transgene Vaccination Using Attenuated S. typhimurium*; Cell, vol. 91, pp. 765–775.

Galan et al. (1990) *Cloning and characterization of the asd gene of Salmonella tyhpimurium: use in stable maintenance of recombinant plasmids in Salmonella vaccine strains*; Gene, vol. 94, pp. 29–35.

Jagusztyn–Krynicka et al. (1982) *Expression of Streptococcus mutans Aspartate–Semialdehyde Dehydrogenase Gene Cloned into Plasmid pBR322*; J. Gen. Microbiol. vol. 28; pp. 1135–1145.

Kahn et al. (1979) *Plasmid Cloning Vehicles Derived from Plasmids ColE1, F, R6K, and RK2*; Methods in Enzymology, vol. 68, pp. 268–280.

Kleckner et al. (1977) *Genetic Engineering in Vivo Using Translocatable Drug–resistance Elements*; J. Mol. Biol. vol. 116, pp. 125–159.

(Continued)

*Primary Examiner*—Rodney P Swartz
*Assistant Examiner*—Khatol Shahnan-Shah
(74) *Attorney, Agent, or Firm*—Thompson Coburn, LLP

(57) ABSTRACT

The invention encompasses methods of maintaining desired recombinant genes in a genetic population of cells expressing the desired gene. The methods utilize microbial cells that have an inactivating mutation in a native essential gene encoding an enzyme which catalyzes a step in the biosynthesis of diaminopimelic acid (DAP). The cells also have an extrachromosomal vector that includes the desired gene and which is capable of homologous recombination with a chromosome of the microorganism. The vector also has a recombinant complementing gene encoding a functional replacement of the native essential gene. The cells of the invention are particularly useful for components of vaccines, including DNA vaccines.

24 Claims, 18 Drawing Sheets

OTHER PUBLICATIONS

Nakayama et al. (1988) *Construction of an ASD+ Expression–Cloning Vector*; Biotechnol., vol. 6, pp. 693–697.

Robinson (1997) *Nucleic acid vaccines: an overview*; Vaccine, vol. 15, No. 8, pp. 785–787.

Sizemore et al. (1995) *Attenuated Shigella as a DNA Delivery Vehicle for DNA–Mediated Immunization*; Science vol. 270; pp. 299–302.

Ulmer et al. (1996) *DNA Vaccines Promising: A New Approach to Inducing Protective Immunity'*; ASM News vol. 62, pp. 476–479.

Ulmer et al. (1996) *DNA vaccines*; Curr. Opin. Immunol. vol. 8, pp. 531–536.

Whalen (1996) *DNA Vaccines for Emerging Infectious Diseases: What if?;* Emerg. Infec. Dis. vol. 2, pp. 168–175.

* cited by examiner

A

```
   1 ggatcttccc taaatttaaa tataaacaac gaattatctc cttaacgtac gttttcgttc
  61 cattggccct caaacccta attaggatca ataaaacagc gacggaaatg attcccttcc
 121 taacgcaaat tccctgataa tcgccactgg actttctgct tgcgcggtaa ggcaggataa
 181 gtcgcattac tgatggcttc gctatcattg attaatttca cttgcgactt tggctgcttt
 241 ttgtatggtg aaggatgcgc cacaggatac tggcgcgcat acacagcaca tctctttgca
 301 ggaaaaaaac gctatgaaaa atgttggttt tatcggctgg cgcggaatgg tggctctgt
 361 tctcatgcaa cgcatggtag aggagcgcga tttcgacgct attcgcctg ttttctttc
 421 tacctcccag tttggacagg cggcgcccac cttcggcgac acctccaccg gcacgctaca
 481 ggacgctttt gatctggatg cgctaaaagc gctcgatatc atcgtgacct gccagggcgg
 541 cgattatacc aacgaaattt atccaaagct gcgcgaaagc ggatggcagg gttactggat
 601 tgatgcggct tctacgctgc gcatgaaaga tgatgccatt attattctcg acccggtcaa
 661 ccaggacgtg attaccgacg gcctgaacaa tggcgtgaag acctttgtgg gcggtaactg
 721 taccgttagc ctgatgttga tgtcgctggg cggtctcttt gccataatc tcgttgactg
 781 ggtatccgtc gcgacctatc aggccgcctc cggcggcggc gcgcgccata tgcgcagct
 841 gttaacccag atgggtcagt tgtatggcca tgtcgccgat gaactggcga cgccgtcttc
 901 cgcaattctt gatattgaac gcaaagttac ggcattgacc cgcagcggcg agctgccggt
 961 tgataacttt ggcgtaccgc tggcgggaag cctgatcccc tggatcgaca aacagctcga
1021 taacggccag agccgcgaag agtggaaagg ccaggcggaa accaacaaga ttctcaatac
1081 tgcctctgtg attccggttg atggtttgtg tgtgcgcgtc ggcgcgctgc gctgtcacag
1141 ccaggcgttc accatcaagc tgaaaaaaga ggtatccatt ccgacggtgg aagaactgct
1201 ggcggcacat aatccgtggg cgaaagtggt gccgaacgat cgtgatatca ctatgcgcga
1261 attaaccccg gcggcggtga ccggcacgtt gactacgccg gttggtcgtc tgcgtaagct
1321 gaacatgggg ccagagttct tgtcggcgtt taccgtaggc gaccagttgt tatggggcgc
1381 cgccgagccg ctcgtcgaa tgctgcgcca gttggcgtag tggctattgc agcgcttatc
1441 gggcctgcgt gtggttctgt aggccggata aggcgcgtca gcgccgccat ccggcgggga
1501 aatttgtgtt aaaccagggg tgcatcgtca cccttttttt gcgtaataca ggagtaaacg
1561 cagatgtttc atttttatca ggagttaagc agagcattgg ctattcttta agggtagctt
1621 aatcccacgg gtattaagcc taacctgaag gtaggacgac gcagatagga tgcacagtgt
1681 gctgcgccgt tcaggtcaaa gaagtgtcac tacctgatgt tgaattggaa gatcc
```

B

MVKDAPQDTGAHTQHISLQEKNAMKNVGFIGWRGMVGSVLMQRMVEERDFDAIRPVFFSTSQFGQA
APTFGDTSTGTLQDAFDLDALKALDIIVTCQGGDYTNEIYPKLRESGWQGYWIDAASTLRMKDDAI
IILDPVNQDVITDGLNNGVKTFVGGNCTVSLMLMSLGGLFAHNLVDWVSVATYQAASGGGARHMRE
LLTQMGQLYGHVADELATPSSAILDIERKVTALTRSGELPVDNFGVPLAGSLIPWIDKQLDNGQSR
EEWKGQAETNKILNTASVIPVDGLCVRVGALRCHSQAFTIKLKKEVSIPTVEELLAAHNPWAKVVP
NDRDITMRELTPAAVTGTLTTPVGRLRKLNMGPEFLSAFTVGDQLLWGAAEPLRRMLRQLA

```
                  DraI
                   |
        10         |  20          30          40          50          60
GGATCTTCCCTAAATTTAAATATAAACAACGAATTATCTCCTTAACGTACGTTTTCGTTC 70         80          90         100         110         120
CATTGGCCCTCAAACCCCTAATTAGGATCAATAAAACAGCGACGGAAATGATTCCCTTCC 130        140         150         160         170         180
TAACGCAAATTCCCTGATAATCGCCACTGGACTTTCTGCTTGCGCGGTAAGGCAGGATAA

AseI
                                 |
       190        200         210|         220         230         240
GTCGCATTACTGATGGCTTCGCTATCATTGATTAATTTCACTTGCGACTTTGGCTGCTTT

BssHII
                                           |
       250              260              270|         280
TTGT ATG GTG AAG GAT GCG CCA CAG GAT ACT GGC GCG CAT ACA CAG
     Met Val Lys Asp Ala Pro Gln Asp Thr Gly Ala His Thr Gln
     __a___a___a___a___a_ASD SPLIT]___a___a___a___a___a___

290         300         310         320         330
CAC ATC TCT TTG CAG GAA AAA AAC GCT ATG AAA AAT GTT GGT TTT
His Ile Ser Leu Gln Glu Lys Asn Ala Met Lys Asn Val Gly Phe
__a___a___a___a___a___ASD [SPLIT]_a___a___a___a___a___a___

340         350         360         370
ATC GGC TGG CGC GGA ATG GTC GGC TCT GTT CTC ATG CAA CGC ATG
Ile Gly Trp Arg Gly Met Val Gly Ser Val Leu Met Gln Arg Met
__a___a___a___a___a___ASD [SPLIT]_a___a___a___a___a___a___

380         390         400         410         420
GTA GAG GAG CGC GAT TTC GAC GCT ATT CGC CCT GTT TTC TTT TCT
Val Glu Glu Arg Asp Phe Asp Ala Ile Arg Pro Val Phe Phe Ser
__a___a___a___a___a___ASD [SPLIT]_a___a___a___a___a___a___
```

```
                               NarI
                                |
                              KasI
                              | |
       430         440        | |    450          460
ACC TCC CAG TTT GGA CAG GCG GCG CCC ACC TTC GGC GAC ACC TCC
Thr Ser Gln Phe Gly Gln Ala Ala Pro Thr Phe Gly Asp Thr Ser
 __a___a___a___a___a___ASD [SPLIT]_a___a___a___a___a___a__

470         480         490         500         510
ACC GGC ACG CTA CAG GAC GCT TTT GAT CTG GAT GCG CTA AAA GCG
Thr Gly Thr Leu Gln Asp Ala Phe Asp Leu Asp Ala Leu Lys Ala
 __a___a___a___a___a___ASD [SPLIT]_a___a___a___a___a___a__

520         530         540         550         560
CTC GAT GATCTATGAAGAGGTGACGTC ATG AAC AAA GGT GTA ATG CGA CCG
Leu Asp                        Met Asn Lys Gly Val Met Arg Pro
 __a__                          __c___c___c_XYLE_c___c___c__

PvuII
                  |
       570        |     580         590         600
GGC CAT GTG CAG CTG CGT GTA CTG GAC ATG AGC AAG GCC CTG GAA
Gly His Val Gln Leu Arg Val Leu Asp Met Ser Lys Ala Leu Glu
 __c___c___c___c___c___c__XYLE___c___c___c___c___c___c__

610         620         630         640         650
CAC TAC GTC GAG TTG CTG GGC CTG ATC GAG ATG GAC CGT GAC GAC
His Tyr Val Glu Leu Leu Gly Leu Ile Glu Met Asp Arg Asp Asp
 __c___c___c___c___c___c__XYLE___c___c___c___c___c___c__

660         670         680         690
CAG GGC CGT GTC TAT CTG AAG GCT TGG ACC GAA GTG GAT AAG TTT
Gln Gly Arg Val Tyr Leu Lys Ala Trp Thr Glu Val Asp Lys Phe
 __c___c___c___c___c___c__XYLE___c___c___c___c___c___c__

700         710         720         730         740
TCC CTG GTG CTA CGC GAG GCT GAC GAG CCG GGC ATG GAT TTT ATG
Ser Leu Val Leu Arg Glu Ala Asp Glu Pro Gly Met Asp Phe Met
 __c___c___c___c___c___c__XYLE___c___c___c___c___c___c__

750         760         770         780
GGT TTC AAG GTT GTG GAT GAG GAT GCT CTC CGG CAA CTG GAG CGG
Gly Phe Lys Val Val Asp Glu Asp Ala Leu Arg Gln Leu Glu Arg
 __c___c___c___c___c___c__XYLE___c___c___c___c___c___c__
```

Figure 6B
(Con't.)

```
                      NdeI
                       |
                       |
790          800          810          820          830
GAT CTG ATG GCA TAT GGC TGT GCC GTT GAG CAG CTA CCC GCA GGT
Asp Leu Met Ala Tyr Gly Cys Ala Val Glu Gln Leu Pro Ala Gly
___c___c___c___c___c___c___XYLE___c___c___c___c___c___c___

NaeI
                                 |
                                 |
    840          850  |       860          870
GAA CTG AAC AGT TGT GGC CGG CGC GTG CGT TCC AGG CCC TCC GGG
Glu Leu Asn Ser Cys Gly Arg Arg Val Arg Ser Arg Pro Ser Gly
___c___c___c___c___c___c___XYLE___c___c___c___c___c___c___

880          890          900          910          920
CAT CAC TTC GAG TTG TAT GCA GAC AAG GAA TAT ACT GGA AAG TGG
His His Phe Glu Leu Tyr Ala Asp Lys Glu Tyr Thr Gly Lys Trp
___c___c___c___c___c___c___XYLE___c___c___c___c___c___c___

930          940          950          960
GGT TTG AAT GAC GTC AAT CCC GAG GCA TGG CCG CGC GAT CTG AAA
Gly Leu Asn Asp Val Asn Pro Glu Ala Trp Pro Arg Asp Leu Lys
___c___c___c___c___c___c___XYLE___c___c___c___c___c__·c___

970          980          990          1000         1010
GGT ATG GCG GCT GTG CGT TTC GAC CAC GCC CTC ATG TAT GGC GAC
Gly Met Ala Ala Val Arg Phe Asp His Ala Leu Met Tyr Gly Asp
___c___c___c___c___c___c___XYLE___c·__c___c___c___c___c___

NaeI                        StyI
       |                            |
       |                            |
    1020          1030          1040|         1050
GAA TTG CCG GCG ACC TAT GAC CTG TTC ACC AAG GTG CTC GGT TTC
Glu Leu Pro Ala Thr Tyr Asp Leu Phe Thr Lys Val Leu Gly Phe
___c___c___c___c___c___c___XYLE___c___c___c___c___c___c___

1060         1070         1080         1090         1100
TAT CTG GCC GAA CAG GTG CTG GAC GAA AAT GGC ACG CGC GTC GCC
Tyr Leu Ala Glu Gln Val Leu Asp Glu Asn Gly Thr Arg Val Ala
___c___c___c___c___c___c___XYLE___c___c___c___c___c___c___
```

Figure 6B
(Con't.)

```
                              HincII
                                |
                             AccI
                              ||
                      SalI   |  StyI
                       |    ||   |
    1110             |1120   |        1130              1140
    CAG TTT CTC AGT CTG TCG ACC AAG GCC CAC GAC GTG GCC TTC ATT
    Gln Phe Leu Ser Leu Ser Thr Lys Ala His Asp Val Ala Phe Ile
    ___c___c___c___c___c___c__XYLE____c___c___c___c___c___c__

1150            1160           1170          1180           1190
    CAC CAT CCG GAA AAA GGC CGC CTC CAT CAT GTG TCC TTC CAC CTC
    His His Pro Glu Lys Gly Arg Leu His His Val Ser Phe His Leu
    ___c___c___c___c___c___c__XYLE____c___c___c___c___c___c__

1200           1210           1220           1230
    GAA ACC TGG GAA GAC TTG CTT CGC GCC GCC GAC CTG ATC TCC ATG
    Glu Thr Trp Glu Asp Leu Leu Arg Ala Ala Asp Leu Ile Ser Met
    ___c___c___c___c___c___c__XYLE____c___c___c___c___c___c__

EcoRV
                                   |
                         ClaI      |
                          |        |
    1240             1250|         |   1260           1270           1280
    ACC GAC ACA TCT ATC GAT ATC GGC CCA ACC CGC CAC GGC CTC ACT
    Thr Asp Thr Ser Ile Asp Ile Gly Pro Thr Arg His Gly Leu Thr
    ___c___c___c___c___c___c__XYLE____c___c___c___c___c___c__

BstEII
                                                                |
         1290           1300            1310             |   1320
    CAC GGC AAG ACC ATC TAC TTC TTC GAC CCG TCC GGT AAC CGC AAC
    His Gly Lys Thr Ile Tyr Phe Phe Asp Pro Ser Gly Asn Arg Asn
    ___c___c___c___c___c___c__XYLE____c___c___c___c___c___c__

BstEII
                                                                |
                                                          AgeI  |
                                                            |   |
    1330           1340           1350           1360        1370 |
    GAA GTG TTC TGC GGG GGA GAT TAC AAC TAC CCG GAC CAC AAA CCG
    Glu Val Phe Cys Gly Gly Asp Tyr Asn Tyr Pro Asp His Lys Pro
    ___c___c___c___c___c___c__XYLE____c___c___c___c___c___c__
```

Figure 6B
(Con't.)

```
                                   PvuII
                                    |
        1380          1390          |    1400          1410
   GTG ACC TGG ACC ACC GAC CAG CTG GGC AAA GCC TTC TTT TAC CAC
   Val Thr Trp Thr Thr Asp Gln Leu Gly Lys Ala Phe Phe Tyr His
   ___c___c___c___c___c___c__XYLE____c___c___c___c___c___c___

1420          1430          1440          1450
   GAC CGC ATT CTC AAC GAA CGA TTC ATG ACC GTG CTG ACC
   Asp Arg Ile Leu Asn Glu Arg Phe Met Thr Val Leu Thr
   ___c___c___c___c___c__XYLE____c___c___c___c___c___

BstEII
                                                      |
   1460          1470          1480          1490     1500 |
   TGATGGTCCGGAGATC ATC ACT ATG CGC GAA TTA ACC CCG GCG GCG GTG
                    Ile Thr Met Arg Glu Leu Thr Pro Ala Ala Val
                 ___b___b___b__ASD [SPLIT]_b___b___b___b___

HincII
           |
   1510    |   1520          1530          1540          1550
   ACC GGC ACG TTG ACT ACG CCG GTT GGT CGT CTG CGT AAG CTG AAC
   Thr Gly Thr Leu Thr Thr Pro Val Gly Arg Leu Arg Lys Leu Asn
   _b___b___b___b___b__ASD [SPLIT]_b___b___b___b___b___b___

1560          1570          1580          1590
   ATG GGG CCA GAG TTC TTG TCG GCG TTT ACC GTA GGC GAC CAG TTG
   Met Gly Pro Glu Phe Leu Ser Ala Phe Thr Val Gly Asp Gln Leu
   _b___b___b___b___b__ASD [SPLIT]_b___b___b___b___b___b___

NarI
           |
          KasI
          ||
   1600   ||     1610          1620          1630          1640
   TTA TGG GGC GCC GCC GAG CCG CTG CGT CGA ATG CTG CGC CAG TTG
   Leu Trp Gly Ala Ala Glu Pro Leu Arg Arg Met Leu Arg Gln Leu
   _b___b___b___b___b__ASD [SPLIT]_b___b___b___b___b___b___

1650          1660          1670          1680
   GCG TAGTGGCTATTGCAGCGCTTATCGGGCCTGCGTGTGG
   Ala
```

Figure 6B
(Con't.)

```
       1690      1700      1710      1720      1730      1740
TTCTGTAGGCCGGATAAGGCGCGTCAGCGCCGCCATCCGGCGGGGAAATTTGTGTTAAAC 1750      1760      1770      1780      1790      1800
CAGGGGTGCATCGTCACCCTTTTTTTGCGTAATACAGGAGTAAACGCAGATGTTTCATTT 1810      1820      1830      1840      1850      1860
TTATCAGGAGTTAAGCAGAGCATTGGCTATTCTTTAAGGGTAGCTTAATCCCACGGGTAT 1870      1880      1890      1900      1910      1920
TAAGCCTAACCTGAAGGTAGGACGACGCAGATAGGATGCACAGTGTGCTGCGCCGTTCAG 1930      1940      1950      1960
GTCAAAGAAGTGTCACTACCTGATGTTGAATTGGAAGATCC
```

Figure 6B
(Con't.)

Nucleotide sequences of trc promoter/operator and MCS

MCS: NcoI EcoRI --------HindIII pYA3098, pYA3148, pYA3332, pYA3333, pYA3334, pYA3336, pYA3339, pYA3340, pYA3341, pYA3342

```
                     -35
5' ATTCTGAAATGAGCTGTTGACAATTAATCATCCGGCTC

-10
GTATAATGTGTGGAATTGTGAGCGGATAACAATTTCACAC
```

| SD | NcoI | EcoRI | | | | Smal | |
|---|---|---|---|---|---|---|---|
| AGGAAACAGACC | ATG | G | | GC | AAT | TCC CGG | GGA |
| | Met | Gly | Ile | Arg | Asn | Ser Arg | Gly |

| BamHI | SalI | | PstI | | | | HindIII | |
|---|---|---|---|---|---|---|---|---|
| TCC | GTC | GAC | CTG | CAG | CCA | AGC | TCC CAA | GCT T 3' |
| Ser | Val | Asp | Leu | Gln | Pro | Ser | Ser Gln | Ala |

Figure 7

**Level of Asd sythesized in recombinant
S. typhimurium strains with different Asd+ plasmids**

Cell lysates of S. typhimurium χ4550 with pYA3333 (lane 1),
pYA3334 (lane 2), pYA3342 (lane 3) and pYA3341 (lane 4).
Lane 5 contains molecular weight markers. The arrow indicates
Asd protein band.

Figure 10

FUNCTIONAL BALANCED-LETHAL HOST-VECTOR SYSTEMS

REFERENCE TO GOVERNMENT GRANT

This invention was made with government support under Grant Numbers DE06669 AI24533 and HD29099. The government has certain rights in this invention.

BACKGROUND OF THE INVENTION

1. Field of the Invention

The invention relates to materials and methods for preparing vaccines, and more particularly to genetically engineered microorganisms which are useful to express desired gene products in the immunized animal host because they are balanced lethals which can be maintained as a genetically stable population within the immunized animal host.

2. Description of the Related Art

References Cited:

Amann and Brosius (1985) *Gene* 40:193.
Asturias et al, *Clin Exp Allergy* 27:1307–1313.
Berg and Howe, Eds. (1989) MOBILE DNA, American Society for Microbiology, Washington, D.C.
Buchanan et al. (1987) *Infect. Immun.* 55:1000.
Cardineau and Curtiss (1987) *J. Biol. Chem.* 262:3344.
Curtiss (1965) *J. Bacteriol.* 90:1238.
Curtiss et al. (1982) in Microbial Drug Resistance (S. Mitsuhashi, ed.) vol. 3, pp 15–27.
Curtiss and Kelly (1987) *Infect. Immun.* 55:3035.
Curtiss et al. (1991) p. 169–198 In L. C. Blankinship et al. (eds) *Colonization Control of Human Bacterial Enteropathogens in Poultry*. Academic Press, New York
Darji et al. (1997)*Cell* 91:765–775, 1997.
Dean (1981)*Gene* 15:190.
Detrich et al. (1999)*Immunol. Today* 20:251–253.
Detrich and Globel (2000)*Subcell. Biochem.* 33:541–557.
Dunstan et al. (1996)*Infect. Immun.* 64:2730–2736.
Errington (1986)*J. Gen. Microbiol.* 132:2953–2960.
Galan et al (1990)*Gene,* 94:29–35.
Gebhardt et al. Eds. (1994) METHODS FOR GENERAL AND MOLECULAR BACTERIOLOGY, American Society for Microbiology, Washington, D.C.
Guyer (1983)*Meth. Enzymol.* 101:362.
Herrmann et al. (1999) "DNA Vaccines for Mucosal Immunity," pp. 809–816 in MUCOSAL IMMUNITY Second ed., Ogra, Mestecky, Lamm, Strober, Bienenstock, and McGhee, eds., Academic Press, San Diego, 1628 pp.
Hone et al. (1996) WO96/34631.
Jagusztyn-Krynicka, et al. (1982)*J. Gen. Microbiol.* 128:1135.
Kahn et al. (1979)*Meth. Enzymol.* 68:268.
Kaniga et al. (1991)*Gene* 109:137–141.
Kaniga et al. (1994)*Mol. Microbiol.* 13:555–568.
Kaniga et al. (1998)*Infect. Immun.* 66:5599–5606.
Kleckner et al. (1977)*J. Mol. Biol.* 116:125.
Krieg et al. (1998)*Trends Microbiol.* 6:23–27.
METHODS IN ENZYMOLOGY (Academic Press, Inc.).
Marquez et al (1985)*J. Bacteriol.* 164:379.
Miller, Jeffrey H. (1992) A SHORT COURSE IN BACTERIAL GENETICS, Cold Spring Harbor Laboratory Press.
Miller and Mekalanos (1988)*J. Bacteriol.* 170:2575–2583.
Nakayama et al. (1988)*Biotechnol.* 6:693.
Neidhardt et al., Eds. (1996) ESCHERICHIA COLI AND SALMONELLA: CELLULAR AND MOLECULAR BIOLOGY, second ed., ASM Press, Washington D.C., especially Chapters 27, 110, 124, 141.
O'Brien, S. J., ed., GENETIC MAPS: LOCUS MAPS OF COMPLEX GENOMES: BOOK 2: BACTERIA, ALGAE AND PROTOZOA, Sixth Ed., Cold Spring Harbor Laboratory, 1993.
Olsson et al. (1997)*Clin. Exp. Allergy* 28:984–991.
Pascual et al. (1997)*Behring. Inst. Mitt.* 98:143–152.
Pawelek et al. (1997)*Cancer Res.* 57:4537–44.
Robinson (1997)*Vaccine* 15:785–787.
Roitt et al., *Immunology*:Fourth Edition, C. V. Mosby International Ltd., London 1998.
Saltzman et al. (1996)*Cancer Bio. Ther. Radiol. Pharm.* 11:145–153.
Saltzman et al. (1997)*J Pediatric. Surg.* 32:301–306.
Sambrook et al. (1989) MOLECULAR CLONING, A LABORATORY MANUAL, second ed., Cold Spring Harbor Laboratory Press.
Salyers and Whitt (1994)*Bacterial Pathogenesis: A Molecular Approach*. ASM Press, Washington, D.C.
Schleifer and Kandler (1972) Bacteriol. Rev. 36:407.
Shepard et al. (1980)*Intl. J. Lepr.* 48:371.
Sizemore et al. (1995)*Science* 270:299–302.
Soldatova et al. (1998)*J. Allergy Clin. Immunol.* 101:691–698.
Twardosz et al. (1997)*Biochem Biophys Res Commun* 239:197–204.
Ulmer et a! (1996a) ASM News 62:476–479.
Ulmer et al. (1996b)*Curr. Opin. Immunol.* 8:531–536.
Valenta et at (1998)*Allergy* 53:552–561.
Viera and Messing (1982)*Gene* 19:259–268
Whalen (1996)*Emerg. Infect. Dis.* 2:168–175.
Whittle et al. (1997)*J: Med. Microbiol.* 46:1029–1038.
U.S. Pat. No. 4,190,495.
U.S. Pat. No. 4,424,065.
U.S. Pat. No. 4,550,081.
U.S. Pat. No. 4,888,170.
U.S. Pat. No. 5,006,335.
U.S. Pat. No. 5,294,441.
U.S. Pat. No. 5,278,744.
U.S. Pat. No. 5,387,744.
U.S. Pat. No. 5,389,368.
U.S. Pat. No. 5,424,065.
U.S. Pat. No. 5,468,485.
U.S. Pat. No. 5,527,529.
U.S. Pat. No. 5,643,771.
U.S. Pat. No. 5,656,488.
U.S. Pat. No. 5,672,345.
U.S. Pat. No. 5,840,483.
U.S. Pat. No. 5,851,519.
U.S. Pat. No. 5,855,879.
U.S. Pat. No. 5,855,880.
U.S. Pat. No. 5,888,799.
U.S. Pat. No. 5,980,907.
U.S. Pat. No. 6,024,961.
Related Art:

Genetically engineered microorganisms have widespread utility and importance. One important use of genetically engineered microorganisms is as a live vaccine for inducing immunity. See, e.g., U.S. Pat. Nos. 6,024,961; 4,888,170; 5,389,368; 5,855,879; 5,855,880; 5,294,441; 5,468,485; 5,387,744; 5,840,483, 5,672,345; 5,424,065; 5,888,799; 5,424,065; 5,656,488; 5,006,335; 5,643,771; 5,980,907; 5,851,519; and 5,527,529, all of which are incorporated by reference. When the genetically engineered microorganism is to be utilized as a vertebrate live vaccine, certain considerations must be taken into account. To provide a benefit beyond that of a nonliving vaccine, the live vaccine microorganism must attach to, invade, and survive in lymphoid tissues of the vertebrate and expose these immune effector sites in the vertebrate to antigen for an extended period of time. By this continual stimulation, the vertebrate's immune system becomes more highly reactive to the antigen than with a nonliving vaccine. Therefore, preferred live vaccines are attenuated pathogens of the vertebrate, particularly pathogens that colonize the gut-associated lymphoid tissue (GALT) or bronchial-associated lymphoid tissue (BALT). An additional advantage of these attenuated pathogens over nonliving vaccines is that these pathogens have elaborate mechanisms to gain access to lymphoid tissues, and thus efficient exposure to the vertebrate's immune system can be expected. In contrast, nonliving vaccines will only provide an immune stimulus if the vaccine is passively exposed to the immune system, or if host mechanisms bring the vaccine to the immune system.

Despite their advantages over non-living vaccines, effective live vaccines must ovecome certain obstacles. Genetically engineered microorganisms used as vaccines for antigen delivery must synthesize a gene product from which it derives no benefit, and the high level expression of the recombinant protein may be deleterious to the microorganism. Thus, the genetically engineered microorganism may be at a selective disadvantage relative to the same type of microorganism that does not produce the cloned gene product. As a result, when the vaccine is being manufactured, e.g., in a fermentor during production of the vaccine, spontaneous segregants that have lost the DNA sequence specifying the desired gene product quickly outpopulate the genetically engineered microorganism. This loss of the antigen-producing DNA sequence can also occur to the vaccine after inoculation into the host animal. Therefore, selection mechanisms have been developed which are designed to maintain the antigen-producing DNA sequence in the microorganism population.

One method for applying selective pressure to a bacterial population to maintain production of the desired polypeptide is to insert the recombinant gene encoding the polypeptide in a plasmid that also contains a gene encoding antibiotic resistance. Most cloning vectors currently in use have one or more genes specifying resistance to antibiotics. Thus, antibiotics can be added to the culture medium for growth of genetically engineered microorganisms to kill those bacteria that have lost the recombinant plasmid. This practice has several drawbacks. First, it is expensive to add antibiotics to growth medium. Second, since antibiotic resistance is often based upon the synthesis of drug inactivating enzymes, cells remain phenotypically drug resistant for a number of cell generations after the loss of genes for drug resistance and the linked desired gene. Third, in the case of genetically engineered bacteria to be used as a live vaccine, the United States Department of Agriculture and the Food and Drug Administration have refrained from approving strains which express antibiotic resistance.

An alternative to the use of antibiotic resistance for maintaining a recombinant plasmid and/or a cloned gene in a genetically-engineered microorganism is the use of a mutant microorganism that lacks a critical biosynthetic enzyme, and supplying the wild-type gene for that enzyme on the plasmid cloning vector. See, e.g., Kahn et al (1979) and Dean (1981). Unfortunately, this is impractical in many situations. The use of mutants which are missing enzymes involved in the biosynthesis of amino acids, purines, pyrimidines, and vitamins often does not preclude the growth of these mutants since the end-product of the pathway which is required for growth is often furnished by the environment. For example, inexpensive media used for the growth of recombinant organisms in fermenters often contain these end products. In addition, particularly in the case of live vaccines, the end product may be supplied in vivo by the vaccinated host.

The problems of genetic instability of genetically engineered microorganisms possessing a cloned gene on a plasmid can arguably be alleviated by integrating the cloned gene into the chromosome of the microorganism. However, integration of the recombinant gene into the chromosome overcomes many of the potential benefits of having it reside on the plasmid. For example, control of plasmid copy number by, for example, selection of the plasmid containing the cloned gene provides a mechanism for increasing the product yield. It is to be noted that the level of expression of a gene is usually proportional to gene copy number, which increases with increasing plasmid copy number. The use of plasmids with a regulatable promoter also offer one mechanism for temporally controlling the expression of the product so that high level expression occurs at less deleterious times during the growth cycle.

All bacteria have a peptidoglycan layer of the cell wall that imparts shape and rigidity. The peptidoglycan is made of a polymer of repeating muramic acid-N-acetylglucosamine units and is cross-linked by short peptides. In all Gram-negative bacteria and in *Mycobacterium* and in *Nocardia* species of *Eubacteria*, the peptide is composed of L-alanine, D-glutamic acid, mesodiaminopimelic acid (DAP), and D-alanine. In most Gram-positive microorganisms the DAP component is replaced by its decarboxylation product L-lysine.

As illustrated by FIG. 1, DAP is synthesized in six enzymatic steps from β-aspartic semialdehyde, which, in turn, is synthesized in two steps from L-aspartic acid. In the first step, L-aspartic acid is phosphorylated by one of several (usually three) β-aspartokinases which are encoded by several (usually three) separate genes regulated independently by repression and/or feedback inhibition of the gene products by the ultimate end products L-threonine, L-methionine, and L-lysine. β-aspartyl phosphate is converted in one step to β-aspartic semialdehyde by β-aspartate semialdehyde dehydrogenase, the product of the asd gene. Mutants with a point mutation in or deletion of the asd gene as well as mutants with mutations in any of the six genes specifying the enzymes for converting β-aspartate semialdehyde to DAP require DAP in all media. When DAP-requiring mutants are deprived of DAP they undergo DAP-less death and lysis, releasing their contents.

The inclusion of asd, and thus dap, mutations in strains of bacteria affords biological containment, since such mutant strains are unable to survive in environments other than a carefully controlled laboratory environment. The basis for this has been extensively described in U.S. Pat. No. 4,190,495.

The gene for β-aspartate semialdehyde dehydrogenase from *Streptococcus mutans* PS14 (UAB62) has been cloned and expressed in asd mutants of *E. coli* (Jagusztyn-Krynicka, et al, 1982; Curtiss et al, 1982). Subsequently, the *S. mutans* asd gene was sequenced (Cardineau and Curtiss, 1987). The gene for β-aspartate semialdehyde dehydrogenase from *Salmonella typhimurium* has also been cloned and expressed in asd mutants of *E. coli* (Galán et al., 1990). Subsequently, the *S. typhimurium* asd gene was sequenced (SEQ ID NO:1) and its amino acid sequence determined (SEQ ID NO:2). Both sequences are found in Genbank accession number AF 015781.

U.S. Pat. No. 5,672,345 discloses a method of maintaining a desired recombinant gene in a genetic population of bacterial cells expressing the product of the desired recombinant gene. The method utilizes host cells having a mutation in a chromosomal gene encoding an enzyme that catalyzes a step in the biosynthesis of an essential cell wall component such as DAP. The host cells are transformed with two recombinant genes in physical linkage: one gene encoding a polypeptide that functionally replaces the enzyme and the other gene encoding the desired gene product. Loss of the recombinant gene complementing the mutant host gene causes the bacterial cells to lyse when in an environment requiring expression of the enzyme. The specification of patent 5,672,345 teaches that it is preferable that the nonfunctional chromosomal gene lack homology with its complementing plasmid gene, or have an extensive enough mutation (e.g., by utilizing a deletion mutation which eliminates the entire gene and/or flanking sequences) to preclude the ability of the complementing plasmid gene from recombining to replace the defective chromosomal gene by two crossover events on either side of the defective chromosomal gene. Such a lack of recombination maximizes the stability of the gene encoding the desired gene product by maintaining the linked selective pressure with the complementing recombinant plasmid gene.

However, avoiding homology between both sides of the inactivating chromosomal gene mutation and its functional plasmid counterpart precludes the use of many useful combinations of these genes. Therefore, it would be desirable to be able to utilize mutant chromosomal genes with complementing plasmid genes having such homology.

SUMMARY OF THE INVENTION

Briefly, therefore, the inventor has succeeded in discovering that balanced-lethal host-vector systems, similar to those described in U.S. Pat. No. 5,672,345, may usefully comprise an extrachromosomal vector that has homology with both sides of the chromosomal mutation that inactivates the native gene which is complemented in the vector. Such homology allows a double crossover to occur between these homologous regions, permiting replacement of the defective chromosomal gene with the active recombinant copy on the vector. In most useful situations, the homology resides between regions flanking the inactivating mutation and its complementing plasmid gene. These flanking regions would often be outside of the inactivated chromosomal gene, particularly if the chromosomal gene is inactivated by a deletion. Preferably, the plasmid also comprises a desired gene, providing linkage between the complementing plasmid gene and the desired gene. The desired gene encodes a desired polypeptide, for example an antigen. This invention provides for the utilization of complementing genes that have this mutation-flanking homology to its inactivated chromosomal counterpart.

Also discovered and disclosed herein is means to reduce the level of expression of the complementing recombinant gene on the vector to the lowest level needed for complementation and to preclude lysis of the bacteria when the complementing plasmid recombinant gene is expressed. This is accomplished through the selective use of particular origins of replication that set particular plasmid copy numbers in conjunction with changes in the regulatory DNA sequences 5' to the complementing recombinant gene. In one aspect of all these embodiments, the −35 recognition sequence and promoter −10 sequence of the complementing recombinant gene is absent. When such vectors have a high copy number origin of replication and are transfected into a microorganism lacking a functional asd gene, enough asd is made from the vector to allow synthesis of sufficient DAP to maintain viability of the microorganism. The above means for reducing the level of the essential gene can be utilized in any of the embodiments described below.

The present invention also teaches the means to generate defined deletions of the native essential gene and to insert therein a gene encoding a protein that can be detected to verify the presence of the mutant chromosomal gene.

Accordingly, the present invention is directed to a microorganism with a cell wall comprising diaminopimelic acid (DAP). The microorganism further comprises (a) an inactivating mutation in a native chromosomal essential gene encoding an essential enzyme which catalyzes a step in the biosynthesis of DAP; (b) a recombinant complementing gene encoding a functional replacement for the essential enzyme, where the complementing gene is on an extrachromosomal vector that is capable of homologous recombination with the chromosome; and (c) a desired gene on the extrachromosomal vector, where the desired gene is a recombinant gene encoding a desired gene product. In progeny populations of the microorganism, the desired gene is stably maintained. Preferably, the microorganism is a bacterium and the extrachromosomal vector is a plasmid. In many embodiments, the bacterium is a member of the *Enterobacteriaceae*. The bacterium is often an attenuated derivative of a pathogenic *Salmonella* that attaches to, invades and persists in the gut-associated lymphoid tissue or bronchial-associated lymphoid tissue. The bacterium is often attenuated through the use of inactivating mutations in native genes. Preferred attenuating mutations are in the following genes:a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and combinations thereof. The most preferred attenuating mutations are aroA, aroC, aroD, cdt, cya, crp, phoP, phoQ, ompR, galE, and htrA.

The microorganisms of the present invention may be utilized to induce an immune response in a vertebrate that has been inoculated with them. In these embodiments, the microorganism is preferably a member of the *Enterobacteriaceae*, most preferably, the attenuated *Salmonella* described above. The most preferred *Salmonella* species are *S. typhimurium, S. typhi, S. paratyphi, S. choleraesuis, S. dublin* and *S. gallinarum*. As is known, each of these *Salmonella* species may have prefered host species, where wild-type strains are pathogenic. See, e.g., U.S. Pat. Nos. 5,468,485 and 4,550,081. Also, the desired gene product in these embodiments is preferably an antigen. Preferred antigens are bacterial antigens, viral antigens, fungal antigens, parasitic antigens, gamete-specific antigens, allergens, and tumor antigens.

Preferred genes that encode the essential enzymes of the above-described bacteria are dapA, dapB, dapD, dapE, and dapF. The most preferred essential gene is a β-aspartic semialdehyde dehydrogenase gene, denoted asd. Preferred inactivating mutations in these genes are deletions and insertions, for example transposon insertions and insertions with a gene encoding a phenotypically detectable reporter gene. Preferred inactivating mutations are mutations that do not normally revert to wild type, such as Tn10 insertions, insertions of a xylE gene, and deletion mutations such as ΔasdA16, ΔasdA1, ΔasdA13 and ΔasdA4.

The desired gene can also be operably linked to a eukaryotic promoter, preferably a CMV promoter, to create a eukaryotic expression vector that serves as a DNA vaccine where the desired gene is transcribed and translated directly by the vertebrate. The DNA vaccine can be introduced into the vertebrate directly or it can be delivered to the vertebrate by live microorganisms such as the *Enterobacteriaceae* described herein.

The present invention is also directed to the recombinant vectors, preferably plasmids, which are useful in the above microorganisms. As indicated previously, the preferred recombinant complementing gene in those plasmids are asd genes. In more preferred embodiments the asd is from a member of the *Enterobacteriaceae*, such as *Salmonella typhimurium*. When the desired gene on the plasmid encodes an antigen, preferred antigens are colonization antigens, i.e. virulence antigens, generally on the surface of pathogens, that promote the ability of a pathogen to infect an animal or human host. Examples include adhesins and invasins (Salyers and Whitt, 1994). Other preferred desired genes encode products that affect vertebrate immunity, such as lymphokines, cytokines, and sperm-specific or egg-specific autoantigens.

Additionally, the present invention is directed to methods of selecting for the presence of a desired gene in a population of microbial cells. The methods comprise (a) transfecting a microbial cell with a plasmid as described above, the microbial cell having an inactivating mutation in a native chromosomal gene encoding the essential enzyme, as previously discussed; and (b) culturing the microbial cell.

Preferred embodiments of these methods utilize microbial cells that are members of the *Enterobacteriaceae* and essential genes that are dap or asd genes. Additionally, the microbial cells may usefully be attenuated derivatives of pathogenic *Salmonella* that attach to, invade and persist in the gut-associated lymphoid tissue or bronchial-associated lymphoid tissue. As previously discussed, when these attenuated strains are the above attenuated *Salmonella*, preferred attenuating mutations are in the following genes: a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and combinations thereof.

The microbes useful for these methods also may have any of the characteristics previously discussed. The culturing of these microbes may be in a vertebrate or in vitro.

Additionally, the present invention is directed to a vaccine for immunization of a vertebrate. The vaccine comprises live bacterial cells of an attenuated derivative of a pathogenic bacterium in a pharmaceutical carrier. The bacterial cells are as previously described, with any of the appropriate features and limitations discussed above. Preferably, the extrachromosomal vector is a plasmid, the bacterium is a *Salmonella*, and the essential gene is an asd gene. The complementing gene may be from the same *Salmonella* species as the bacterial cell. For these embodiments, the desired gene product is an antigen, as previously described. An additional embodiment of the invention is thus a method of inducing immunoprotection in a vertebrate, where the method comprises administering to the vertebrate the vaccine described above. The vaccines of these embodiments can be utilized as DNA vaccines when the desired gene is operably linked to a eukaryotic promoter, for example a CMV promoter. As previously discussed, these DNA vaccines can be delivered by bacteria or by direct introduction of the DNA into the vertebrate.

In additional embodiments, the present invention is directed to a method of delivering a desired gene product to a vertebrate. The method comprises administering to the vertebrate live bacterial cells of an attenuated derivative of a pathogenic bacterium. The bacterial cells are as described above. In these embodiments the preferred bacteria are *Salmonella*, most preferably *S. typhimurium, S. typhi, S. paratyphi, S. choleraesuis, S. dublin* or *S. gallinarum*. As before, preferred attenuating mutations are in a pab gene, a pur gene, an aro gene, asd, a dap gene, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hiLA, rpoE, flgM, tonB, slyA, and combinations thereof, and the most preferred essential gene is an asd. Preferred desired gene products in these embodiments include antigens, lymphokines, cytokines, and sperm-specific or egg-specific autoantigens.

Other embodiments of the invention include the various novel plasmids and bacterial strains first described herein.

BRIEF DESCRIPTION OF THE DRAWINGS

FIGS. 2A and 2B illustrate the nucleotide (SEQ ID NO:1) and encoded amino acid sequence (SEQ ID NO:2), respectively, of the *Salmonella typhimurium* asd, gene showing from 5' to 3': an upstream nucleotide sequence of 244 base pairs (bp); an open reading frame (ORF) of 1176 bp containing two EcoRV sites (indicated by underlining) separated by 729 bp; and a downstream sequence of 315 bp; with the start and stop sites indicated by bold letters.

FIG. 6B shows the nucleotide (SEQ ID NO:3) and encoded amino acid sequences (SEQ ID NO:4) of this genetic construct, showing from 5' to 3': the 244 bp asd upstream sequence, an ORF containing the first 273 bases of the 5' portion of the asd4 ORF encoding SEQ ID NO:5 (marked as "a" along the bottom of the sequence), a 955 bp fragment of the xylE gene, which encodes SEQ ID NO:6 and which replaces a deletion of the asdA gene between the EcoRV sites (marked as "c"), a 174 bp region from the 3' portion of the asdA ORF (marked as "b"); and the 315 base pair asdA downstream sequence (SEQ ID NO:7). Various restriction sites are also shown in FIG. 6B.

FIG. 7 depicts the trc promoter and the multiple cloning site present in pYA3332, pYA3333, pYA3334, pYA3341 and pYA3342 (SEQ ID NO:8).

FIG. 10 depicts a SDS polyacrylamide gel of extracts of *S. typhimurium* strains after staining with Coomassie Brilliant Blue to reveal the level of Asd protein specified by the Asd⁺plasmids pYA3333, pYA3334, pYA3342 and pYA3341.

DETAILED DESCRIPTION OF THE INVENTION

A. Definitions

Figure 1:
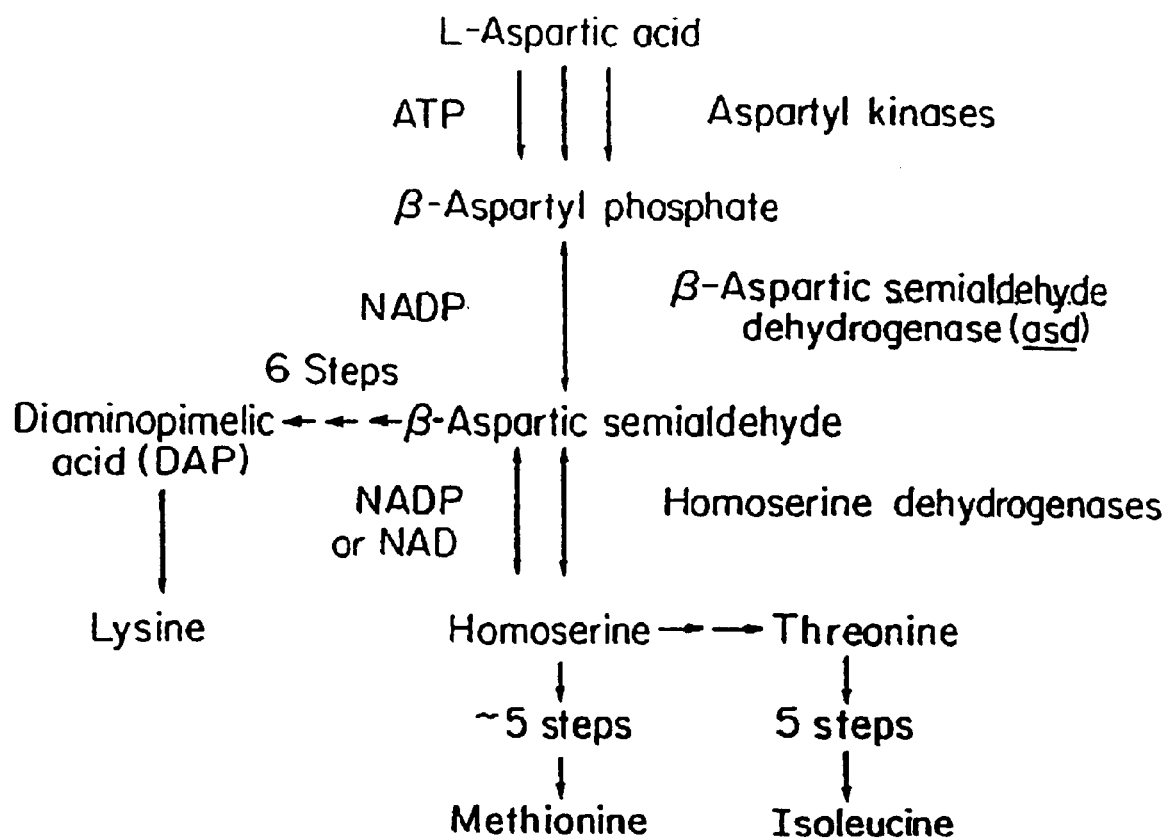
FIG. 1 is a flow chart for the biosynthesis of the aspartic acid family of amino acids.

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation.

A "progeny population" means the population of living bacterial cells in a culture propagated from a single, recombinant bacterial cell. Unless otherwise defined, a recombinant gene on an extrachromosomal vector is "stably maintained" in a progeny population when the majority of the cells in a population lacking a native essential gene complemented by the recombinant gene are both able to survive in a particular environment (e.g., lacking diaminopimelic acid (DAP)) and retain and/or express a desired gene that is linked to the recombinant gene. Preferably, at least 90% of the cells in the population survive and retain the desired gene; more preferably, at least 99% of the cells survive.

"Control sequence" refers to a DNA sequence that is necessary to effect the expression of a coding sequence to which it is operably linked. As such, control sequences provide sites for the action of repressors, activators, enhancers, RNA polymerase, and other transcription factors. Nonlimiting examples of control sequences are promoters, ribosome binding sites, transcription terminator sequences, and translation stop sequences.

Control sequences permitting expression of gene products in bacteria are distinctly different from control sequences necessary for gene expression in eukaryotic organisms such that prokaryotic control sequences generally do not function in eukaryotic cells and vice versa. The term "control sequence" can encompass those sequences from prokaryotes or eukaryotes.

"Operably linked" refers to a juxtaposition wherein the components so described are in a relationship permitting them to function in their intended manner. A control sequence "operably linked" to a coding sequence is present in the cell in such a way that expression of the coding sequence may be influenced by the action of the control sequence.

"Gram-negative bacteria" include cocci, nonenteric rods, enteric rods and spirilla. Non-limiting examples of genera of Gram-negative bacteria include *Neisseria, Spirillum. Pasteurella, Brucella, Yersinia, Francisella, Haemophilus, Bordetella, Escherichia, Salmonella, Shigella, Klebsiella, Bartonella, Ehrlichia, Legionella, Enterobacteria, Proteus, Vibrio, Pseudomonas, Xanthomonas, Myxococcus, Erwinia, Bacteroides, Acetobacter, Aerobacter, Agrobacterium, Azotobacter, Spirilla, Serratia, Vibrio, Rhizobium, Chlamydia, Rickettsia, Trepanema, Fusobacterium, Borrelia* and *Trepanema*.

"Gram-positive bacteria" include cocci, nonsporulating rods, and sporulating rods. Non-limiting examples of genera of Gram-positive bacteria include *Actinomyces, Bacillus, Clostridium, Corynebacterium, Erysipelothrix, Lactobacillus, Listeria, Mycobacterium, Nocardia, Staphylococcus, Streptococcus,* and *Streptomyces*.

A "mutation" is an alteration of a polynucleotide sequence, characterized either by an alteration in one or more nucleotide bases, or by an insertion of one or more nucleotides into the sequence, or by a deletion of one or more nucleotides from the sequence, or a combination of these.

A "gene" is a biological unit of heredity. Generally, a gene is a polynucleotide sequence that encodes an RNA molecule or a polypeptide, or a mutation of said polynucleotide sequence. The gene may be a naturally occurring sequence that is capable of being expressed into an active or inactive polypeptide. The gene may also comprise a mutation, for example a point mutation, insertion, or deletion, such that it is not capable of being expressed, or such that it expresses an altered or truncated polypeptide or RNA molecule. A gene may be created by recombinant DNA methodologies. Alternatively, the gene may be synthesized by well-known synthetic methods.

A "native gene" is a gene as it occurs in a wild-type organism, for example, the gene encoding β-aspartic semialdehyde dehydrogenase (Asd) in *E. coli* or *Salmonella*, the genes encoding alanine racemase, and the genes encoding D-alanyl-D-alanine ligase. Other examples of native genes are described infra.

A "recombinant gene," as used herein, is defined as an identifiable polynucleotide sequence within a larger polynucleotide sequence that is not found in that form and position in the larger sequence in nature. The recombinant gene can be, for example, a wild-type gene that is inserted in a non-native position in the chromosome, or a mutant form of the wild-type gene in the native position. As used herein, recombinant genes are the product of genetic engineering manipulations performed in vitro.

As used herein, "recombination" or "genetic recombination" is the joining or exchange of portions of two DNA molecules within a living cell. In homologous recombination, the joining or exchange occurs where the two DNA molecules are homologous. The exchange can occur by way of a single crossover (i.e., point of exchange) between the two molecules. Alternatively, the exchange can occur between two separate homologous regions of either or both of the molecules (double crossover). Non-homologous recombination may be mediated by genetic elements such as transposons.

An "essential gene" is a gene that encodes a function that is required for cell viability. Essential genes may be functional, that is they are providing the essential function. Essential genes may also be non-functional, for example by having mutations that render the translated protein non-functional, or by not being operably linked to a control element essential for transcription of the gene. There also may be more than one functional copy of an essential gene in a microbial cell, for example one gene on a plasmid and the other on the chromosome. As such, the loss of any one copy of the essential gene would not be fatal to the cell.

Unless otherwise indicated, essential genes of the present invention encode an enzyme that catalyzes a step in the biosynthesis of diaminopimelic acid (DAP), an essential cell wall component in many microbes. An example of an essential gene is asd, encoding β-aspartic semialdehyde dehydrogenase. Microbes which are deficient in asd gene function will grow on media containing DAP, L-methionine and L-threonine, or DAP and homoserine.

An "essential cell wall component" is one that is necessary to maintain the structural integrity of the cell wall. Examples of essential cell wall components of prokaryotes include glycans, particularly peptidoglycans. While the use of genes encoding enzymes for bacterial cell wall synthesis are exemplified herein, the skilled artisan would recognize that the methods provided herein can be utilized with other prokaryotic cell wall containing organisms.

A "peptidoglycan" is a typical constituent of cell walls of almost all prokaryotic cells. These molecules are responsible for the rigidity of the cell wall. Peptidoglycans are a family of macromolecules containing acylated amino sugars and three to six different amino acids; the heteropolymers contain glycan strands crosslinked through short peptides. Peptidoglycans have been reviewed in Schleifer and Kandler (1972).

As used herein, "DAP" refers to both stereoisomers of diaminopimelic acid and its salts, i.e., both the LL- and meso-forms, unless otherwise shown by specific notation.

The gene symbols for mutant strains utilized herein are those described by O'Brian (1993), and Sanderson et al., Chapter 110 in Neidhardt et al., 1996. The symbols used for transposons, particularly Tn10, follow the convention used in Altman et al., Chapter 141 in Neidhardt et al., 1996.

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

"Transfection" or "transformation," as used herein, refers to the insertion of an exogenous polynucleotide into a host cell, irrespective of the method used for the insertion, for example, direct uptake (naturally or by electroporation), transduction, or conjugation. The exogenous polynucleotide may be maintained as a plasmid, or alternatively, may be integrated into the host chromosome.

By "vaccine" is meant an agent used to stimulate the immune system of a living organism so that protection against harm is provided. Immunization refers to the process of rendering an organism immune to a disease, or treating a disease, by exposing the organism to an antigen that stimulates the organism's immune system to recognize a component of the disease. As used herein, "immune system" refers to anatomical features and mechanisms by which a multicellular animal reacts to an antigen. As is well known, the vertebrate humoral immune system results in the elicitation of antibodies that specifically bind to the antigen. The antibody so produced may belong to any of the immunological classes, such as immunoglobulins A, D, E, G or M. Of particular interest are vaccines that stimulate production of immunoglobulin A (IgA) since this is the principal immunoglobulin produced by the secretory system of warm-blooded animals. However, vaccines of the present invention are not limited to those that stimulate IgA production. For example, vaccines of the nature described infra are likely to produce a range of other immune responses in addition to IgA formation, for example, cellular immunity. Immune response to antigens is well studied and widely reported. A survey of immunology is given in Roitt et al., (1998). Unless otherwise indicated, "vaccines" are live bacteria that express or deliver antigens or genetic material encoding antigens to which immune responses are desired.

A "vertebrate" is any member of the subphylum Vertebrata, a primary division of the phylum Chordata that includes the fishes, amphibians, reptiles, birds, and mammals, all of which are characterized by a segmented bony or cartilaginous spinal column. All vertebrate species have a functional immune system and respond to antigens by cellular and/or humoral immune responses. Thus all vertebrates are capable of responding to vaccines. Although vaccines are most commonly given to mammals, such as humans or dogs (rabies vaccine), vaccines for commercially raised vertebrates of other classes, such as the fishes and birds, are contemplated as being within the scope of the present invention.

"Attenuated" refers to a pathogenic microorganism having mutations which reduce the ability of the pathogen to elicit disease symptomology and disease in an individual, but which do not eliminate the potential of the attenuated bacterium to attach to, invade and persist in appropriate lymphoid tissues within the individual. Attenuated microbes are useful, for example, to expose an organism to a particular gene product, such as an antigen or a therapeutic protein, over an extended time period. "Attenuated" does not mean that a microbe of that genus or species cannot ever function as a pathogen, but that the particular microbe being used is attenuated with respect to the particular animal being tested. Attenuated host cells of the present invention may belong to a genus or species that is normally pathogenic. As used herein, "pathogenic" means capable of causing disease or impairing normal physiological function. Attenuated strains are incapable of inducing a full suite of symptoms of the disease that is normally associated with its pathogenic counterpart. Sometimes "avirulent" is used as a substitute term for attenuated.

As used herein, "microbe" or "microorganism" includes bacteria, protozoa, and unicellular fungi.

As used herein, "DNA vaccine" refers to a DNA molecule, preferably a plasmid, that has a gene sequence encoding a desired gene product operably linked to a eukaryotic control sequence, so that the desired gene product is expressed maximally after introduction of the DNA vaccine internally into eukaryotic cells by vaccination (immunization). The DNA vaccine can be administered to individuals to be immunized by injection, air gun or preferably by use of attenuated bacteria that liberate the DNA vaccine on entrance into host cells of the immunized individual. See, e.g., Detrich et al. (1999); Detrich and Globel (2000); Herrmann et al., (1999); Krieg et al. (1998); Ulmer et al. (1996a); Ulmer et al. (1996b).

B. General Description

Unless otherwise indicated, the practice of the present invention employs conventional techniques of cell culture, molecular biology, microbiology, recombinant DNA manipulation, immunology and animal science, which are within the skill of the art. Such techniques are explained fully in the literature. See, e.g., DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Hames and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R. L. Rodriguez and D. T. Denhardt, eds., 1987, Butterworths); Sambrook et al. (1989), MOLECULAR CLONING, A LABORATORY MANUAL, second ed., Cold Spring Harbor Laboratory Press; and Ausubel et al. (1995), SHORT PROTOCOLS IN MOLECULAR BIOLOGY, John Wiley and Sons.

This invention is directed to genetically engineered microbial host cells that stably maintain a desired recombinant gene in progeny populations. The host cells in this population have an inactivating mutation in a native essential gene encoding an enzyme that is essential for cell survival in that the enzyme catalyzes a step in the biosynthesis of an essential cell wall component. In addition, a recombinant complementing essential gene, genetically linked to a desired gene product, replaces the function of the inactivated essential gene. The invention describes methods for creating and isolating cells that are suitable host cells. Also disclosed are extrachromosomal vectors, particularly plasmids, which are suitable for transfecting microbial host cells. These plasmids comprise the recombinant complementing gene and the gene encoding the desired gene product. The cells of the invention are particularly suitable as components of vaccines, particularly live vaccines.

The cells of the invention are also suitable for the production of DNA vaccines which themselves can be used after isolation from the cells for direct immunization of individuals by recently developed DNA vaccine technologies (Ulmer et al., 1996a; Ulmer et al., 1996b; Whalen, 1996; Robinson, 1997). In these embodiments, the DNA vaccines are preferably produced as high copy number plasmid vectors in $E.\ coli$, where they can be easily purified by well known methods. It is also possible to use attenuated derivatives of bacterial pathogens to deliver DNA vaccine vectors to cells within the immunized individual (Sizemore et al., 1995; Hone et al., 1996; Pascual et al., 1997; Darji et al., 1997).

One characteristic of the host cells of the invention is that their cell walls contain a peptidoglycan comprised of diaminopimelic acid (DAP), which is necessary to maintain the structural integrity of the cell, i.e., without which the cell lyses, a victim of DAPless death. Examples of host cells in which the peptidoglycan is comprised of DAP are known to those of skill in the art, for example, see Schleifer and Kandler (1972), and include, for example probably all Gram-negative bacteria, as well as other organisms, such as Gram-positive bacteria in the genera *Mycobacterium* and *Nocardia*. A review of the methods by which a peptidoglycan may be characterized as containing DAP is presented in Schleifer and Kandler (1972).

Another characteristic of the host cells of the present invention is that they have been mutated so that a native chromosomal essential gene encoding an enzyme which catalyzes a step in the biosynthesis of DAP is not functional, i.e., does not yield a functional enzyme. Methods for mutating cells to create the host cells of the invention are known in the art, and include, for example, chemical mutagenesis, UV mutagenesis, mutations induced via the action of transposons, or defined deletion mutations using recombinant techniques. See, e.g., Curtiss, U.S. Pat. No. 5,672,345; Miller (1992); Gebhardt et al. (1994); Miller and Mekelanos (1988) and Methods in Enzymology. Although host cells carrying point mutations in the above-described genes are included in the invention, it is preferable to use host cells carrying deletion mutations in these genes, since deletion mutants do not generally revert.

Enzymes which catalyze the biosynthesis of DAP are known in the art. FIG. 1 shows the pathway for the biosynthesis of the aspartate family of amino acids, of which both stereoisomers of DAP are members. For a review of the biosynthesis of this family of amino acids, see Umbarger, chapter 27 in Neidhardt et al.(1996). Examples of genes encoding enzymes which catalyze steps in the biosynthesis of DAP are known in the art for a variety of organisms, see, for example, GENETIC MAPS 1987 (S. J. O'Brien, ed., Cold Spring Harbor Laboratories), and include, for example, the dapA, dapB, dapC, dapD, and dapE and dapF genes in *S. typhimurium* and in *E. coli*. Another enzyme which is essential for DAP synthesis is β-aspartic semialdehyde dehydrogenase (Asd), which is encoded by the asd gene.

Described in the Examples, infra, are methods for introducing deletion mutations in the above genes, particularly the asd gene (Δasd), in a diversity of bacterial strains, particularly members of the *Enterobacteriaceae*. Also described are methods to isolate asd mutants of other Gram-negative bacteria and mycobacteria. Table 1 lists the *E. coli* K-12 and *S. typhimurium* strains used to isolate asd mutants and their derivatives; the Asd strains listed therein are examples of strains which can be used to construct other strains, utilizing transposon techniques and also molecular genetic techniques for allele replacement, as described infra. Asd strains are also described in U.S. Pat. Nos. 4,190,495, 5,672,345 and 5,840,483.

TABLE 1

Bacterial strains

| Strain number | Parent strain/ plasmid | Relevant genotype | Derivation |
|---|---|---|---|
| A. *Escherichia coli* strains | | | |
| χ2108 | K-12/F⁻ | leu-50 tsx-98 proB59 Δ69[lacZOPI] Δ40[gal-uvrB] rposL206 asdA4 argH70 | HNO2-induced Asd⁻ mutant of χ2087 |
| χ2637 | K-12/F⁻ | tsx-63 purB41 glnV42 λ⁻ pyrF30 his-53 tte-1 ΔasdA4 xyl-14 cycB2 cycA1 | Plcml(χ2108) → χ660 with sel'n for AroB⁺ Asd⁻ |
| χ2978 | K-12/F⁻ | tsx-63 purE41 glnv42 λ⁻ pyrF30 his-53 tte-1 zhf-2::Tn10 xyl-14 cycB2 cycA1 | P1L4(χ2842::Tn10 library) χ2637 with sel'n for Tcʳ Asd⁺ |

TABLE 1-continued

Bacterial strains

| Strain number | Parent strain/ plasmid | Relevant genotype | Derivation |
|---|---|---|---|
| χ2979 | K-12/F⁻ | tsx-63 purE41 glnv42 λ⁻ pyrF30 his-53 tte-1 ΔasdA4 zhf-2::Tn10 xyl-14 cycB2 cycA1 | P1L4(χ2978) → χ2637 with sel'n for Tc$^r$ |
| χ2981 | K-12/F⁻ | Δ41[proB-lacYZ] glnV42 λ⁻ tte-1 ΔasdA4 zhf-2::Tn10 cycA1 | P1L4(χ2979) → χ354 with sel'n for Tc$^r$ Asd⁻ |
| χ2984 | K-12/F⁻ | Δ41[proB-lacYZ] λ⁻ tte-1 ΔasdA4 Δ[zhf-2::Tn10] cycA1 | FA$^r$Tc$^s$ derivative of χ2981 |
| JM83 | K-12/F⁻ | ara Δ[lac-pro] λ⁻ rpsL thi ø80dlacZ ΔM15 | Viera and Messing |
| χ6096 | K-12/F⁻ | ara Δ[lac-pro] rpsL ΔasdA4 zhf-2::Tn10 thi ø80dlacZ ΔM15 | P1L4(χ2981) → JM83 with sel'n for Tc$^r$ Asd⁻ |
| χ6097 | K-12/F⁻ | ara Δ[lac-pro] rpsL ΔasdA4 Δ[zhf-2::Tn10] thi ø80dlacZ ΔM15 | FA$^r$Tc$^s$ derivative of χ6096 |
| χ6212 | K-12/F⁻ | ΔglnV44 [lacZYA-argF]U169 λ⁻ø80d lacZ ΔM15 gyrA recA1 relA1 endA1 ΔasdA4 Δ[zhf-2::Tn10] hsdR17 | DH5α |
| Y1090 | K-12/F⁻ | ΔaraD139 ΔlacU169 Δlon tyrT trpC22::Tn10 rpsL hsdR (pBR322 lacI$^q$) | Promega Biotech |
| MGN-617 | K-12/F⁻ | thr-1 lenB6 lacY1 recA RP4-2- Tc::Mu λpir ΔasdA4 | Sm10 λpir |

B. *Salmonella typhimurium* strains

| | | | |
|---|---|---|---|
| χ3000 | LT2-Z/ pStLT100 | prototroph, suppressor-free | Curtiss collection |
| χ3008 | LT2-Z/ pStLT100 | asdA15 | HNO$_2$-induced Asd⁻ mutant of χ3000 |
| χ3013 | LT2-Z/ pStLT100 | zhf-1::Tn10 | from P22(λ3000::Tn10 library) → χ3008 with sel'n for Tc$^r$ Asd⁺ |
| χ3021 | LT2-Z/ pStLT100 | Δ[zhf-1::Tn10] ΔasdA1 P22⁺ | FA$^r$Tc$^s$ derivative of χ3013 |
| χ3385 | LT2-Z | hsdL6 galE596 trpB2 flaA66 his-6165 rpsL120 xyl-404 metE551 metA22 lamB⁺ (*E. coli*) Δzja::Tn10 hsdSA29 val | cured derivative of AS68 (E. T. Palva) |
| χ3520 | LT2-Z/ pStLT100 | ΔasdA1 zhf-4::Tn10 | P22HTint(χ3536) → χ3021 with sel'n for Tc$^r$ (asd⁻); P22HTint(χ3021 Tc$^r$ asd⁻)$^a$ → χ3000 with sel'n for Tc$^r$ (Asd⁻) |
| χ3536 | LT2-Z/ pStLT100 | zhf-4::Tn10 | from P22HTint(χ3324::Tn10 library) → χ3000; P22HTint(χ3000::Tn10 library) → χ3021 with sel'n for Tc$^r$ Asd⁺; P22HTint(χ3021 Tc$^r$)$^a$ → χ3000 with sel'n for Tc$^r$ |
| χ3537 | LT2-Z/ pStLT100 | zhf-3::Tn10 | from P22HTint(χ3324::Tn10 library) → χ3000; P22HTint(χ3000:Tn10 library) → χ3021 Tc$^{ra}$ → χ3000 with sel'n for Tc$^r$ |
| χ3628 | LT2-Z/ pStLT100 | Δ[zhf:3::Tn10] ΔasdA13 | FA$^r$Tc$^s$ Asd⁻ derivative of χ3537 |
| χ3629 | LT2-Z | hsdL6 Δ[galE-uvrB]-1005 flaA66 rpsL120 zhf-3::Tn10 xyl-404 lamB⁺ (*E. coli*) Δ[zja::Tn10] hsdSA29 | P22HTint(χ3537) → χ3477 with sel'n for Tc$^r$ Asd⁺ |
| χ3630 | LT2-Z | hsdL6 Δ[galE-uvrB]-1005 flaA66 rpsL120 ΔasdA13 xyl-404 lamB⁺ (*E. coli*) Δ[zja::Tn10] hsdSA29 | P22HTint(χ3628) →χ3629 with sel'n for Fa$^r$ Asd⁺ |
| χ3638 | LT2-Z | hsdL6 Δ[galE-uvrB]-1005 flaA66 rpsL120 zhf-4::Tn10 xyl-404 lamB⁺ (*E. coli*) Δ[zja::Tn10] hsdSA29 | P22HTint(χ3536) → χ3477 with sel'n for Tc$^r$ Asd⁺ |
| χ3656 | LT2-Z/ pStLT100 | leu hsdLT galE trpD2 rpsL120 ΔasdA1 zhf-4::Tn10 metE551 metA22 hsdSA hsdSB ilv | P22HTint(X3520) → χ3179 with sel'n for Tc$^r$ Asd⁻ |
| χ3761 | UK-1 | prototroph | Curtiss et al. (1991) |
| χ4064 | SR-11/ pStSR100 | gyrA1816 Δcya-1 Δcrp-1 | FA$^r$Tc$^s$ derivative of χ4055 (Curtiss and Kelly, 1987) |
| χ4070 | SR-11/ pStSR100 | gyrA1816 Δcya-1 Δcrp-1 ΔasdA1 zhf-4::Tn10 | P22HTint(χ3520) → χ4064 with sel'n for Tc$^r$ Asd⁻ |
| χ4072 | SR-11/ pStSR100 | gyrA1816 Δcya-1 Δcrp-1 ΔasdA1 Δ[zhf-4::Tn10] | FA$^r$Tc$^s$ derivative of χ4070 |

TABLE 1-continued

Bacterial strains

| Strain number | Parent strain/ plasmid | Relevant genotype | Derivation |
|---|---|---|---|
| χ4550 | SR-11/ pStSR100 | gyrA1816 ΔasdA1 Δ[zhf-2::Tn10] Δcrp-1 Δcya-1 | P22HT int (χ3520) → χ4064 followed by sel'n for $FA^R TC^S (Asd^-)$ |
| χ8315 | UK-1 | ΔphoPQ23 ΔasdA20::xylE | MGN-762 |
| DB9031 | LT2-Z/ pStLT100 | zeh-4::Tn10 | Tn10 95% linked to gyrA |
| MGN-023 | UK-1 | ΔasdA16 | χ3761 |
| MGN-762 | HK-1 | ΔphoPQ23 | χ3761 |
| MGN-1036 | UK-1 | ΔpoxA270 | χ3761 |

[a]Since χ3021 is lysogenic for P22, P22 HT int was propogated on the χ3021 rtransductant following UV-induction (15 sec at 5 $J/m^2$) of the prophage. The resulting lysate was used to transduce χ3000.

Standard mutagenesis and mutant enrichment protocols are not efficient for the recovery of asd mutants, since desired mutants (requiring DAP) undergo lysis and death in the absence of DAP. Thus, previously isolated asd mutants were discovered indirectly and by chance, or by brute-force screening of millions of potential mutants. The invention encompasses an efficient procedure for the selective enrichment and isolation of asd mutants.

In a synthetic medium, asd mutants require L-methionine, L-threonine, and DAP for growth. The requirement for L-methionine and L-threonine is satisfied by homoserine, which is a common precursor to both methionine and threonine (see FIG. 1). Mutagenesis of an E. coli or S. typhimurium strain followed by an ampicillin-cycloserine procedure for the enrichment of auxotrophic mutants seldom, if ever, recovers mutants with a sole requirement for homoserine. Curtiss et al (1965) describe a cycloserine-enrichment procedure for selecting auxotrophs, and a modification of that procedure also employing ampicillin is included in the Examples of U.S. Pat. No. 5,672,345. The reason that homoserine-requiring auxotrophs are seldom isolated is that β-aspartate semialdehyde is converted to homoserine by either of two dehydrogenases which are encoded in two genes. The probability of inactivating both genes in a single cell is exceedingly small, and thus the homoserine-requiring auxotrophs may not be detected by random screening techniques.

This problem is overcome by the discovery that the inclusion of DAP in all media during mutagenesis, and enrichment or selection using the ampicillin-cycloserine technique, leads to the recovery of asd mutants that require both homoserine and DAP. Ampicillin and cycloserine both inhibit cell wall synthesis in growing cells capable of protein synthesis, but are without effect on auxotrophic mutants unable to synthesize proteins because of the absence of nutritional requirements. The asd mutant strains χ3008 and χ2108 (see Table 1), which are S. typhimurium and E. coli strains, respectively, were isolated using this procedure. The $Asd^-$ phenotype of χ3008 is due to a point mutation in the asd gene, and thus the frequency of reversion to $Asd^+$ is fairly high. On the other hand, the $Asd^-$ phenotype of χ2108 results from a deletion in the asd gene resulting in an undetectable reversion frequency.

Strains carrying mutations of the asd gene, particularly desirable deletion mutations, can be generated by techniques utilizing transposons as described in U.S. Pat. No. 5,672,345. Transposons can be added to a bacterial chromosome at many points. The characteristics of transposon insertion and deletion have been reviewed in Kleckner (1977). For example, the transposon Tn10, which confers resistance to tetracycline (and sensitivity to fusaric acid) can be used to create Δasd mutants in a variety of bacterial species, including, for example, E. coli and S. typhimurium (EPO Pub. No. 315,682; U.S. Pat. Nos. 5,387,744; 5,672,345).

One method for creating Δasd mutants in E. coli and S. typhimurium is described in the Examples of U.S. Pat. No. 5,672,345. First, a library of random Tn10 insertions in the chromosomes of the bacteria is created utilizing an appropriate transposon vector, for example, λNK561 for E. coli (Kleckner et al., 1977) with a λ-sensitive strain of S. typhimurium, an example of which is χ3385(Table 1). A suitable transducing phage, for example, PIL4 or P22HT int, for E. coli and S. typhimurium, respectively, which has been propagated on the Tn10 library in the appropriate species, is used to transduce $Asd^-$ mutants of that species, and bacteria containing an $Asd^+Tc^r$ phenotype are selected. Examples of useful $Asd^-$ strains are the E. coli strain χ2108, and the S. typhimurium strain χ3008 (see Table 1). Since single events are more probable than double events, most transductants, for example χ2978 and χ3013 (see Table 1) will have Tn10 closely linked to the asd gene. Selection for fusaric acid resistance, which results from deletion of Tn10 and adjacent DNA sequences, yields Δasd mutants in which all or portions of the closely linked asd gene have been deleted. The ΔasdA1 mutation in the S. typhimurium χ3021 strain was isolated from χ3013 (Table 1) using this procedure.

Deletion mutations can also be introduced into the bacterial chromosome by using recombinant DNA techniques. For example, a specific portion of the asd gene can be deleted from pYA272 or similar plasmid, and the derived plasmid introduced into an $Asd^+$ S. typhimurium strain to allow for homologous recombination leading to cells that have the genetically engineered Δasd mutation in the chromosome as well as in the plasmid. The culture is then grown at elevated temperatures, for example, 43° C., in the presence of low concentrations of novobiocin, plated on medium devoid of antibiotics, and then replica plated to medium containing ampicillin to identify clones that have lost the recombinant plasmid derived from pUC18, which confers resistance to ampicillin. See, e.g., Example 17 of U.S. Pat. No. 5,672,345, describing the cloning of the asd gene of S. typhimurium into pUC 18 to yield pYA272 following subcloning and transposon mutagenesis to delimit the extent of the S. typhimurium asd gene in pYA275.

i of defined deletion (Δ) mutations may be facilitated by using a pir-dependent R6K replicon (Miller and Mekalanos, 1988) where the suicide vector is unable to replicate in a cell lacking the pir gene, which is inserted into the chromosome of the donor parent. Selection for allele replacement in the recipient bacterium is enhanced by use of sucrose selection since the sacB gene present on the pir-dependent suicide vector confers sucrose sensitivity to cells that possess the gene (Kaniga et al, 1991). In this case, following a single crossover event to integrate the suicide vector into the chromosome, plating on agar medium in the presence of 5% sucrose selects for loss of the integrated suicide vector, which sometimes will occur by a second recombination event such that the deletion mutation on the original suicide vector replaces the wild-type gene in the chromosome.

When the desired double crossover event to generate a Δasd strain is sufficiently frequent, direct screening for the nutritional requirement imposed by the deletion mutation is a relatively efficient screening process. This screening process can be simplified by the insertion into the defined deletion a reporter gene that would be expressed and recognized by spraying colonies with a chromogenic substrate. Such a construction would also facilitate studies to examine the genetic stability of strains with various deletion mutations in the native essential gene when possessing extrachromosomal vectors that could permit homologous recombination to replace the mutated essential gene with the wild-type complementing gene on the plasmid vector. Such studies are important in validating the utility of a functional balanced-lethal host-vector system when employed for production of products by fermentation or use as vaccines for immunization of animals and humans. A useful gene for this purpose is the xylE reporter gene (Kaniga et al., 1994) since colonies on an agar plate can be sprayed with a 250 mM catechol solution. Colonies that express the xylE gene will turn yellow in about five minutes and the spray does not effect the viability of cells within the colony.

After isolating and characterizing a deletion mutant, it may be advantageous to place a transposon such as Tn10 adjacent to the deletion, by well-known methods, so that the deletion can be moved into other strains. For example, the zhf-2::Tn10 insertion in the E. coli K-12 strain $\chi$6096 (Table 1) can be transduced using standard transduction procedures for PIL4 to introduce the transposon into a great diversity of bacterial strains and species that are transducible with the wide host range generalized transducing phage PIL4. Since tetracycline resistance is associated with sensitivity to fusaric acid, one can take a PIL4 lysate grown on a strain carrying a Δasd mutation, for example, $\chi$2984 (Table 1) and transduce any recipient strain with a construct such as zhf-2::Tn10, followed by selection for fusaric acid resistance. In this case, the Δasd mutation replaces the zhf-2::Tn10. If the recipient strain has a different restriction behavior than E. coli K-12, subjecting the recipient strain to a brief heat shock, for example,5 to 10 min at 45°–50° C., may eliminate this barrier.

An analogous method can be used for isolating Δasd mutants of various strains of S. typhimurium. The generalized transducing phage P22HT int can be grown on strains such as, for example, $\chi$3013, $\chi$3536, or $\chi$3537, which possess zhf-1::Tn10, zhf-4::Tn10, and zhf3::Tn10, respectively (see Table 1). The phage carrying the transposon is then used to transduce other suitable recipient strains to tetracycline resistance. A P22HT int lysate, resulting from propagation of the phage on a bacterial strain carrying a Δasd mutation, for example $\chi$3021 or $\chi$3628, is used to transduce a strain carrying a zhf::Tn10 insertion. Mutants that are resistant to fusaric acid are selected. As with E. coli, the Δasd mutation replaces the inserted $Tn_{10}$.

It should be noted that transduction to insert Δasd mutations as replacements for a zhf::Tn10 insertion, with selection of the desired transductant by its resistance to fusaric acid occurs at a frequency of $10^{-4}$–$10^{-5}$, whereas spontaneous loss of the Tn10 insert by a deletion type mutational event occurs at a frequency of about $10^{-8}$. Thus, the use of transduction with a phage carrying a Δasd gene in the construction of the desired strains ensures the correct genotype with a very low probability for recovery of new deletion mutants.

Many strains of Salmonella are not transducible with phage P22. For example, two of the Tn10 insertions linked to the asd gene, the ΔasdA13 mutation and the ΔasdA4 mutation linked to zhf-4::Tn10 may be placed in Salmonella strains that possess a galE mutation. When these strains, $\chi$3629, $\chi$3638, $\chi$3630 and $\chi$3656, respectively, are grown in the presence of galactose they have a normal smooth lipopolysaccharide coat (LPS) and are sensitive to P22. However, growth in the absence of galactose causes the cells to have a rough coat lacking LPS side chains. Those cells are infectible by PIL4. PIL4 can be propagated on $\chi$3629 (Table 1), and the lysate used to transduce a PIL4 sensitive strain, resulting in a zhf-3::Tn10 insertion into the strain. PIL4 propagated on $\chi$3630, which has the ΔasdA13 mutation, is used to transduce the Tn10 carrying strain, and fusaric acid resistant cells are selected. The result is the introduction of the ΔasdA13 mutation into a new Salmonella strain. Alternatively, PIL4 can be propagated on $\chi$3656 and a suitable recipient transduced to TC$^i$ in the presence of DAP. In this way the ΔasdA4 mutation can be inherited linked to zhf4::Tn10. The zhf-4::Tn10 can then be removed by transduction with PIL4 grown on $\chi$3385 (Table 1) and used to transduce to Tc$^s$ by selecting for fusaric acid resistance.

If transduction of one of the available asd deletion mutations into a species or strain of choice is not feasible or possible, then the strategy previously described for isolation of asd mutants can be employed. A bacterial strain is mutagenized, and mutant enrichment and selection is carried out in the presence of DAP to selectively isolate mutants unable to synthesize homoserine. After obtaining an asd mutation, the reversion frequency of the mutant is determined. If a deletion mutation is desired, it can be done in a variety of ways known in the art, but most simply by introducing a Tn10 transposon library by transduction, selecting for a simultaneous Asd$^+$and Tc$^r$ phenotype. Generally, the Tn10 will be closely linked to the asd gene, and if fusaric acid resistant isolates are selected, deletion of the Tn10 and the adjacent DNA into the asd gene will result in an asd deletion mutation. If the Tn10 procedure does not provide results in a bacterial species, then another transposon can be used to establish linkage to the asd gene; available transposons are known in the art (see Berg & Howe (1989); Craig NL, Chapter 124 in Neidhardt et al. (1986)). The transposon-asd gene complex can be cloned using known genetic engineering techniques. A recombinant can be prepared with precise deletion of the asd gene, the deleted asd gene can then be returned to the wild-type bacterial strain, as described above.

Alternatively, a defined deletion mutation can be generated within a cloned gene sequence using standard molecular genetic manipulations with restriction enzymes and subcloning or by using polymerase chain reaction (PCR) procedures. A mutated allele with a defined deletion can then be introduced into a pir-dependent R6K suicide vector with the sacB genetic determinant conferring sucrose sensitivity and allele replacement selected after transfer of the suicide vector, either by electroporation or conjugation, into the recipient strain of bacteria desired to be mutated.

Another characteristic of the host cells of the invention is that they comprise two recombinant genes. The first recombinant gene, the "complementing gene" or "complementing recombinant gene" or "complementing essential gene" encodes a polypeptide that functionally replaces the enzymatic activity of the inactive native essential gene. For example, an Asd⁻ E. coli cell may be transformed with a recombinant polynucleotide construct encoding the asd gene from S. mutans. See Curtiss et al (1982) for evidence that the S. mutans asd gene product functionally replaces the E. coli gene product.

The above E. coli cells comprising the S. mutans asd complementing essential gene exemplifies another characteristic of the complementing essential gene that is considered desireable, that it does not undergo homologous recombination with the mutant E. coli essential gene because of a lack of sequence homology. The S. mutans asd gene vector pYA292 with mutant asd genes contained in a variety of E. coli and/or S. typhimurium strains with Δasd strains which lack any and all nucleotide sequences contained on pYA292; and a system in which the deletion is partial for the asd structural gene, but extends into its flanking regions. Other examples of genes that can complement an asd mutation are known in the art, and include, for example, the asd gene from B. lactofermentum (Marquez et al (1985). The construction of vectors containing the asd gene from S. mutans, which can be used to transform Asd⁻ strains of E. coli and S. typhimnurium are discussed in the Examples of U.S. Pat. No. 5,672,345, and includes pYA248. Table 1 lists bacterial strains and Table 2 lists strains and plasmids for plasmid constructions.

TABLE 2

Plasmids

| Plasmid | Property | Derivation | Host strain number | Relevant genotype |
|---|---|---|---|---|
| F(traD36 proA⁺ proB⁺ lacI⁹ΔM15) pSGMU37 | 7.6 kb, LacZ⁺ | Errington(1986) | χ6054 | recA1 Δ(lac-pro) endA1 gyrA96 endA1 gyrA96 thi-1 hsdR17 supE44 relA1 |
| pMEG-006 | 3.88 kb, MCS, tetR, tetA, ΔasdA16 | See Example 1 | MGN-617 | see Table 1 |
| pMEG-223 | 8.4 kb, sacR, sacB, Δasd20, xylE | See Example 2 | MGN-617 | see Table 1 |
| pMEG-443 | 9.7 kb, MCS, cat, amp, sacR, sacB, ΔasdA16 | See Example 1 | MGN-617 | see Table 1 |
| pVAX1-asd | 3.7 kb, SD-asd, P$_{CMV}$, MCS | See Example 6 | χ4072 | see Table 1 |
| pYA248 | 3.0 kb, P$_{trc}$ promoter, MCS | U.S. Pat. No. 672,345 | χ4072 | see Table 1 |
| pYA261 | SpaA | U.S. Pat. No. 672,345 | χ4072 | see Table 1 |
| pYA262 | SpaA | U.S. Pat. No. 672,345 | χ4072 | see Table 1 |
| pYA280 | 4.45 kb, MCS, Ap$^r$, asd⁺ | See Example 18 of U.S. Pat. No. 5,672,345 | χ6097 | see Table 1 |
| pYA292 | 3.9 kb, P$_{trc}$ promoter, MCS, lacZ(a), asd⁺, rrnB transcription terminator | See Example 19 of U.S. Pat. No. 5,672,345 | MGN-617 | see Table 1 |
| pYA810 | 3.15 kb, P$_{trc}$ promoter, MCS, lacZ(a), asd⁺, rrnB transcription terminator | See Example 3 | | |
| pYA3137 | 3.5 asd⁺, MCS pUC ori | See Example 4 | MGN-023 | |
| pYA3149 | 3.7 asd⁺, MCS pBR322 ori | See Example 4 | MGN-0223 | |
| pYA3332 | 3.3 kb, asd⁺, MCS, p15A ori | See Example 3 | MGN-023 | see Table 1 |
| pYA3333 | 3.5 kb, asd⁺, MCS, pBR ori | See Example 3 | MGN-023 | see Table 1 |
| pYA3334 | 3.4 kb, asd⁺, MCS, pUC ori | See Example 3 | MGN-023 | see Table 1 |
| pYA3341 | 2.6 kb, asd⁺, MCS, pUC ori, P$_{trc}$ promoter | See Example 4 | MGN-023 | see Table 1 |
| pYA3342 | 2.8 kb, asd⁺, MCS, pBR ori, P$_{trc}$ promoter | See Example 4 | MGN-023 | see Table 1 | sequence, and its lack of homology to the E. coli sequence is reported in Cardineau and Curtiss (1987). The lack of recombination between the host cell gene and the recombinant gene is useful for maintaining the linked selective pressure for the second recombinant gene. One can, however, avoid homologous recombination while using a complementing gene cloned from the desired recipient strain provided that the recipient host has some or all of the nucleotide sequence of the native essential gene and/or flanking sequences deleted so that double crossover recombination with the cloned asd gene in the vector is not possible. Examples of such combinations of a mutant native essential gene and a complementing recombinant essential gene include the S. typhimurium asd gene as contained in the As established herein, host cells of the present invention may also have defined chromosomal deletions of the native essential gene with small regions of homologous DNA sequences in the vector-borne complementing recombinant gene. This could permit either single homologous recombination events or separate homologous recombination events on either side of the inactive native gene. Such events would result in restoration of the chromosomal DAP-prototrophic phenotype due to the presence of copies of the complementing gene present on the chromosome, as well as on the plasmid vector. Even though such recombination events can be theoretically possible, it is established herein that they generally occur at a sufficiently low frequency as to be undetectable. They could possibly be detectable only after long periods of time of the recombinant strains in an immunized animal host or following growth in culture for an excess of 50 generations. In these instances, the utility of the invention is as good as in constructions in which recombination to replace the mutated chromosomal gene is not possible because of a complete absence of nucleotide sequence homology between the plasmid and the chromosome. See, e.g., Example 5, showing that the presence of such regions of homology does not result in detectable loss of expression of the desired gene.

All the genes involved in the biosynthesis of DAP are located in the chromosome and are presumably regulated to some extent by the required amount of DAP needed to support cell wall synthesis which is dependent upon growth rate and conversion to lysine required for protein synthesis. When the gene for one of the enzymes in this pathway is located on a multicopy extrachromosomal vector, as is the complementing recombinant gene of the present invention, it can be expected that the production of that essential enzyme will be far in excess of what is needed to catalyze the required biosynthetic step in the synthesis of DAP. Since the level of enzyme synthesized is more or less proportional to gene copy number, it can be expected that bacterial cells containing such an extrachromosomal vector would produce excess essential enzyme equivalent to the copy number of the vector. For example, the pYA3332 vector (FIG. 8) with its p15A replicon discussed in Example 3 would have 15 to 20 times more Asd protein than necessary. Similarly, the cells with the pYA3333 and pYA3334 Asd$^+$plasmids (FIG. 8) would be expected to synthesize an even greater excess of the Asd protein. Since the overexpression of proteins is of no benefit to a cell and places energy demands for the synthesis of this excess protein on the cell, slower growth results. Thus, the bacterial strain would have a poorer performance when used for any of the potential applications in which a functional balanced-lethal host-vector system would be employed. Therefore, the present invention contemplates the use of origins of replication in the extrachromosomal vectors that result in high copy number of the vector, providing for high expression of the desired gene, but in which expression of the asd gene is reduced, maximizing viability of the host cells. Such constructs are within the skill of the art. Example 4 provides examples of how this can be accomplished. As described therein, eliminating the −35 and −10 promoter sequences for the asd gene still provides for sufficient production of Asd to maintain viability, since sufficient asd mRNA is made by occasional accidental transcription of the asd gene by one or more of the 100 or more plasmid copies present in each cell. Translation of that rare asd mRNA yields just enough Asd enzyme to catalyze the synthesis of a sufficient amount of DAP for cell wall synthesis.

As previously discussed, the host cells of the present invention also have a desired recombinant gene encoding the polynucleotide of a desired gene product such as a polypeptide or a mRNA. The choice of desired gene is not narrowly limited and may include any gene useful in a vaccine, including genes encoding, for example, viral, bacterial, fungal or parasite antigens, cytokines or lymphokines, etc. In preferred embodiments, the expression of the desired gene is dependent on a control sequence linked to the recombinant complementing essential gene. For example, in pYA261 and pYA262 of Example 13 of U.S. Pat. No. 5,672,345, the desired gene spaA is controlled by the P$_{trc}$ promoter. Preferably, the desired gene and the complementing gene are on the same extrachromosomal vector (e.g., plasmid). In this way, loss of the desired gene due to the loss of the extrachromosomal vector will result in lysis of the cell because the complementing gene (encoding an enzyme required for cell wall synthesis) will be lost. Methods of constructing vectors with these characteristics are known in the art using recombinant DNA technology and are discussed more fully in the section on vaccines, infra. See also, e.g., U.S. Pat. Nos. 4,190,495; 4,424,065; 4,888,170; 5,294,441; 5,389,368; 5,468,485; 5,656,488; 5,672,345 5,840,483; 5,855,879; 5,855,880; and 6,024,961. Examples of vectors in which the second gene encodes β-galactosidase, surface protein antigen A (SpaA) of *S. mutans*, and antigens from *M. leprae* are presented in U.S. Pat. No. 5,672,345. However, the choice of the desired gene is not limited to any particular encoded polypeptide that can be produced in the host cell. Included in the Examples section and in U.S. Pat 5,672,345 are expression vectors, generally suitable for insertion of any desired gene by known methods, which contain the *S. mutans* asd gene or the *S. typhimurium* asd gene, which are useful for complementing the Asd phenotype in *S. typhimurium* and in *E. coli*.

In order for the desired gene to be useful in the present invention, the gene must be expressed. Gene expression means that the information encoded in the sequence of DNA bases is transformed into a physical product in the form of a RNA molecule, polypeptide or other biological molecule by the biochemical mechanisms of the cell in which the gene is located. The biological molecule so produced is called the gene product. The term gene product as used here refers to any biological product or products produced as a result of expression of the gene. The gene product may be, for example, an RNA molecule, a peptide, or a product produced under the control of an enzyme or other molecule that is the initial product of the gene, i.e., a metabolic product. For example, a gene may first control the synthesis of an RNA molecule that is translated by the action of ribosomes into an enzyme that controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

The above-described balanced-lethal host vectors are useful as constituents of live vaccines. In these cases, the desired recombinant gene would encode an antigen of a fungal, bacterial, parasitic, or viral disease agent. Live vaccines are particularly useful where localized immunity to the disease agent is important and might be a first line of defense.

The host cells used in live vaccines are attenuated derivatives of pathogens. Most preferably, the attenuated derivatives are able to attach to, invade and persist in the gut-associated lymphoid tissue (GALT) or bronchial-associated lymphoid tissue (BALT). Such attenuated host cells are preferred because they are known to be able to persist in the inoculated animal, causing exposure to the antigen for an extended time period. Such a long exposure period is known to be highly effective in inducing an immunogenic response to the antigen.

Attenuation can be conferred upon the microbes by any known means, including chemical mutagenesis and the use of various recombinant genes. Preferred methods of conferring attenuation render the host cells unable to revert to the virulent condition. The most preferred methods of conferring attenuation on host cells are through the introduction of stable mutations or gene insertions by recombinant methods.

Non-limiting examples of such methods include (1) introducing mutations that impose a requirement for aromatic amino acids and vitamins derived from precursors in this pathway (Stocker et al., 1983, Dev. Biol. Stand. 53:47–54; Hoiseth and Stocker, 1981, Nature 291:238–9); (2) mutating genes for global regulators such as cya and cyp (U.S. Pat. Nos. 5,389,368; 5,855,879; 5,855,880; 5,294,441 and 5,468,485), phoP (U.S. Pat. No. 5,424,065), ompR (Dorman et al., 1989, *Infect. Immun.* 57:2136–40), and poxA (Kaniga et al.( 1998)); (3) mutating genes for lipopolysaccharide (LPS) synthesis, such as galE (Germanier et al., 1975, *J. Infect. Dis.* 131:553–8), although this alone may be insufficient (Hone et al., 1988, *Infect. Immun.* 56:1325–33); (4) mutating genes needed for colonization of deep tissues, such as cdt (U.S. Pat. No. 5,387,744); or (5) by preventing expression of genes for proteases required at high temperature, such as htrA (Johnson et al., 1991, *Mol. Microbiol.* 5:401–7).

Once rendered attenuated, the microbes can serve as the immunogenic component of a vaccine to induce immunity against the microbe. Thus, the use of any microbe possessing the characteristics of the host cells described supra, including non-pathogenicity, are contemplated by this invention, including but not limited to *E. coli, Salmonella spp., E. coli-S. typhimurium* hybrids, *Shigella spp., Yersinia spp., Pasteurella spp., Legionella spp.* or *Brucella spp.* Preferred microbes are members of the genus *Salmonella* such as *S. typhimurium, S. typhi, S. paratyphi, S. gallinarum, S. enteritidis, S. choleraesius, S. arizona*, or *S. dublin*.

In certain embodiments of the invention, the attenuated derivative of a pathogenic microbe (also referred to herein as a carrier bacterium) can be used to deliver selected antigens to the GALT, for example to the Peyer's patches of the ileum. Some genera of bacteria, such as *Salmonella*, are known to home to the Peyer's patches (Carter et al., 1974,*J. Exp. Med.* 139:1189). Also, *S. typhimurium-E. coli* hybrids have also been shown to colonize Peyer's patches in mice (Hohmann, A. W., et al, 1978, *Infect. Immun.* 22:763). By engineering these carrier bacteria to contain and express a recombinant desired gene encoding an antigen from a pathogenic organism, antibodies will be produced against the desired gene product from the pathogen as described in U.S. Pat. No. 5,888,799. As is well known, recombinant DNA techniques now allow the development of totally unique vaccines in which specific antigens are produced by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable of eliciting an autoimmune state.

Thus, the present invention has wide applicability to the development of effective vaccines against bacterial, fungal, parasite or viral disease agents, in which local immunity is important and might be a first line of defense. Nonlimiting examples are vaccines for the control of pneumonic plague caused by *Yersinia pestis*, of gonorrhea caused by *Neisseria gonorrhoeae*, of syphilis caused by *Treponema pallidum*, and of venereal diseases as well as eye infections caused by *Chlamydia trachomatis*. Species of *Streptococcus* from both group A and group B, such as those species that cause sore throat or heart diseases, *Neisseria meningitidis, Mycoplasma pneumoniae, Hemophilus influenza, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholera, Shigella spp., Legionella pneumophila*, and other pathogenic bacteria of the genera of the above organisms are additional, nonlimiting examples of bacteria within the scope of this invention from which genes could be obtained. Viral vaccines, such as those produced against influenza viruses, are also encompassed by this invention. Viral vaccines can also be produced against other viruses, either DNA or RNA viruses. Non-limiting examples include viruses from the classes Papovirus, Adenovirus, Herpesvirus, Poxvirus, Parvovirus, Reovirus, Picornavirus, Myxovirus, Paramyxovirus, Flavivirus or Retrovirus. Vaccines to protect against infection by pathogenic fungi, protozoa and parasites are also contemplated by this invention.

In an additional embodiment, the invention encompasses a vaccine for the immunization of a vertebrate animal. The vaccine comprises a live attenuated derivative of a pathogenic microbe, wherein the derivative is substantially incapable of producing functional adenylate cyclase and AMP receptor protein while being capable of expressing a recombinant gene derived from an organism that is a pathogen of or that produces an allergen of said animal. See, e.g., Valenta et al, *Allergy* 53:552–561. 1998; Olsson et al., *Clin. Exp. Allergy* 28:984–991. 1998; Soldatova et al., *J. Allergy Clin. Immunol.* 101:691–698, 1998; Twardosz et al, *Biochem Biophys Res Commun* 239:197–204, 1997.

In order for a vaccine to be effective in inducing antibodies, the antigenic material must be released in such a way that the antibody-producing mechanism of the vaccinated animal can come into play. Therefore the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of intranasal, although other methods of administering the vaccine, such as intravenous, intramuscular, subcutaneous injection or intramammary or intrapenial or vaginal administration, are possible.

When the attenuated microbe is used as a vaccine, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell.

The use of the avirulent strain with asd mutations and occasional loss of the Asd$^+$cloning vector would permit lysis of approximately 1% of the bacteria during each generation (see examples) to release the cell contents to thus stimulate an immune response against the released cell contents including any colonization and virulence antigens.

In certain embodiments, the host cells of the present invention comprise a desired gene encoding an allergen. A vaccine utilizing those host cells may be used in an exposure regimen designed to specifically desensitize an allergic host. Allergens are substances that cause allergic reactions in an animal that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection to allow the carrier microbe to reach the animal's blood stream may be acceptable. Intravenous, intramuscular or intramammary injection is also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchi of the animal being vaccinated. Preferably, these strains are attenuated derivatives of enteropathogenic strains produced by genetic manipulation of enteropathogenic strains. Strains that home to Peyer's patches and thus directly stimulate production of IgA are most preferred. In animals these include specific strains of *Salmonella*, and *Salmonella-E. coli* hybrids that home to the Peyer's patches.

The dosages required will vary with the antigenicity of the gene product and need only be an amount sufficient to induce an immune response typical of existing vaccines. Routine experimentation will easily establish the required amount. Typical initial dosages of vaccine could be 0.001–0.1 mg antigen/kg body weight, with increasing amounts or multiple dosages used as needed to provide the desired level of protection.

The pharmaceutical carrier in which the vaccine is suspended or dissolved may be any solvent or solid or encapsulated in a material that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc, sucrose, and feed for farm animals. Adjuvants may be added to enhance the antigenicity if desired. When used for administering via the bronchial tubes, the vaccine is preferably presented in the form of an aerosol.

Immunization with a pathogen-derived gene product can also be used in conjunction with prior immunization with the attenuated derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the desired gene product to stimulate the lymphoid cells of the GALT or BALT. The enhanced response is known as a secondary, booster, or anamnestic response and results in prolonged immune protection of the host. Booster immunizations may be repeated numerous times with beneficial results.

In other embodiments of the invention, a recombinant attenuated derivative of a pathogenic microbe can be used to express, in the animal host, gene products that are therapeutic against disease in the inoculated animal. Non-limiting examples of such products include lymphokines or cytokines to modulate the immune response (Saltzman et al. (1996); Saltzman et al. (1997); Whittle et al. (1997); Dunstan et al. (1996)), sperm-specific and egg-specific autoantigens to arrest fertility (U.S. Pat. No. 5,656,488), specific antibodies, e.g., which bind to tumors or pathogens such as viruses, fungi, parasites, or bacteria, or gene products essential for a pathogen to cause disease), or enzymes that have the potential to convert prodrugs into toxic drugs within a tumor cell mass in an individual with a solid tumor (Pawelek et al. (1997)).

Because the avirulent microbes of this invention are able to traverse a variety of immunocompetent structures including the GALT, mesenteric lymph nodes and spleen, such microbes may also be used to modulate the immune system by producing a variety of immunoregulatory products. Accordingly, one or more genes encoding immunoregulatory proteins or peptides may be recombinantly introduced as a desired gene into the attenuated microbes such that the microbes are capable of taking up residence in the appropriate immunocompetent tissue and express the recombinant desired gene product to suppress, augment or modify the immune response in the host. Nonlimiting examples of immunoregulatory molecules include colony stimulating factors (macrophage, granulocyte, or mixed), macrophage chemotoxin, macrophage inhibition factor, leukocyte inhibitory factors, lymphotoxins, blastogenic factor, interferons, and interleukins.

Derivatives of attenuated microbes are also contemplated to be within the scope of this invention. By derivative is meant sexually or asexually derived progeny and mutants of the avirulent strains including single or multiple base substitutions, deletions, insertions or inversions which retain the basic functioning of the host cells previously described. For example, various strains of *Salmonella spp.* carry the gyrA mutation conferring nalidixic acid resistance, which is a convenient marker to enable recovery from infected animals. See, e.g., Example 23 of U.S. Pat. No. 5,672,345, discussing uses of gyrA. However, drug resistance is not a desirable attribute for strains to be used as vaccines. Thus the gyrA mutation can be easily removed by transducing the gyrA+(conferring sensitivity to nalidixic acid) gene into strains by selecting for inheritance of a closely linked Tn10 and then removing Tn10 by selection for fusaric acid resistance, as in strain DB9031 (Table 1).

Deposits of Strains Useful in Practicing the Invention

Deposits of biologically pure cultures of the following strains were made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description.

| Strain | Deposit Date | ATCC No. |
|---|---|---|
| χ6097 containing pYA232 | Oct. 6, 1987 | 67,537 |
| χ2978 | Oct. 6, 1987 | 53,679 |
| χ3520 | Oct. 6, 1987 | 53,681 |
| χ4072 containing pYA248 | Oct. 6, 1987 | 67,538 |
| χ3008 | Oct. 6, 1987 | 53,680 |
| χ2108 | Oct. 6, 1987 | 53,678 |
| χ6097 containing pYA292 | Sep. 26, 1988 | 67,813 |

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

1. Generation of Defined Deletion (Δ) Mutations in the S. typhimurium asd Gene.

The complete nucleotide sequence of the S. typhimurium asd gene and flanking regions is presented in FIG. 2A (SEQ ID NO:1). This sequence includes the 244 bp upstream of the asd sequence, the asd ORF of 1176 bp, and a downstream sequence of 315 bp with start and stop sites indicated by bold letters. The amino acid sequence encoded by the ORF is indicated in FIG. 2B. In Example 6 of U.S. Pat. No. 5,672,345, we described a means to generate Δasd mutations by excision of a Tn10 closely linked to the asd gene. The excision of the Tn10, selected for by selecting for fusaric acid resistance, leads to deletions of all or part of the asd gene and all DNA sequences between the asd gene and the site of the Tn10 insertion. As a consequence, genetic information flanking the asd gene is deleted. This has the potential of attenuating the Δasd Salmonella strain even when an Asd⁺plasmid vector is present. Such potential additional attenuation in conjunction with attenuation due to mutations, such as cya and crp, phoPQ, aroA, C, or D, etc. could result in hyperattenuation and thus reduce immunogenicity of the vaccine strain. Rather than having to contend with such possibilities, it is preferable to generate defined deletion mutations that only lack known DNA sequences that encode a desired gene and no more, in this case the asd gene. One method to generate the defined deletions of the S. typhimurium asd gene is as follows.

Figure 3:
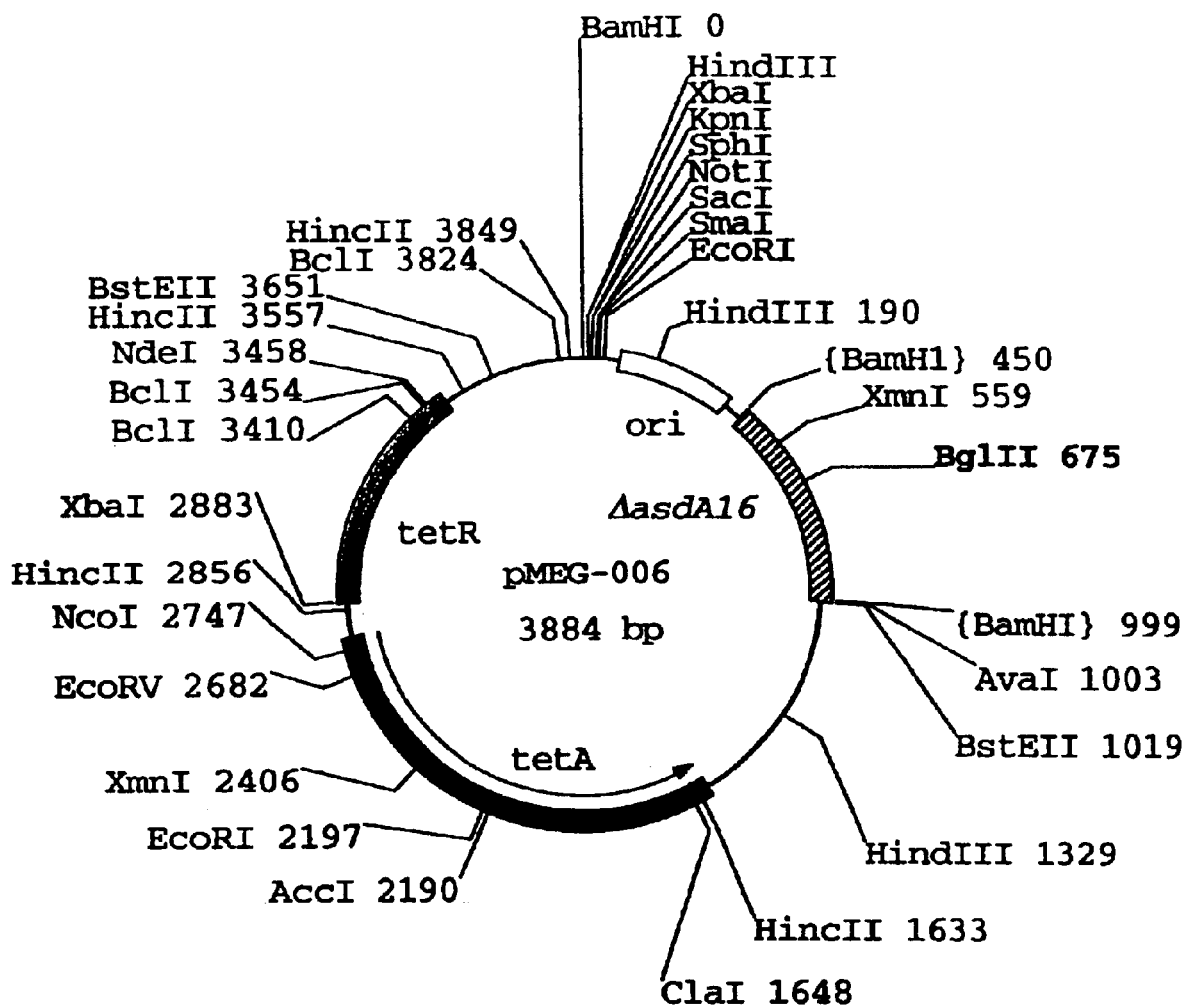
FIG. 3 illustrates the structure of pMEG-006, a pir-dependent suicide vector with the Δasd16 mutation.

The 1.7 kb BglII fragment containing 1735 bp with the asd sequence depicted in FIG. 2B is cloned from pYA292 (FIG. 16 of U.S. Pat. No. 5,672,345) into the BamHI site of the pir-dependent suicide replicon pMEG-002 to generate pMEG-003. This particular suicide vector possesses the tetA and tetR genes conferring tetracycline resistance and confers sensitivity to fusaric acid upon cells possessing this plasmid. Inverse PCR on used on the sequence in pMEG-003 so as to delete base pairs 219 through 1460 in the asd sequence (SEQ ID NO:1; depicted in FIG. 2A) and to insert in its stead a 6-base sequence encoding a BglII restriction enzyme cleavage site. The resulting plasmid pMEG-006 is depicted in FIG. 3. The defined deletion mutation present in pMEG-006, if introduced into the chromosome of a recipient cell, would impose nutritional requirements for DAP and homoserine (or threonine and methionine). pMEG-006 is then introduced by electroporation into the suicide plasmid donor MGN-617 (Table 1) which possesses a λpir prophage to ensure faithful suicide plasmid replication. MGN-617 possesses a Δasd mutation which can be used for counter-selection against the donor after transfer of the suicide vector into a desired recipient strain, usually a derivative of S. typhimurium. In such a mating, tetracycline-resistant DAP-independent isolates are selected which result from a single crossover to integrate pMEG-006 into the chromosome. These isolates are then grown up in L broth and fusaric acid-resistant isolates are selected in the presence of DAP. In some cases the second crossover, which is necessary to eliminate the integrated plasmid to confer fusaric acid resistance, will occur at a second site between the homologous sequences adjacent to the asd gene in the chromosome and the deleted asd sequence in pMEG-006, wherein this second recombination event occurs on the opposite side of the deleted asd sequence than was used for the first recombination event. This results in replacement of the wild-type asd⁺allele in the chromosome for the ΔasdA16 defined deletion allele present in the suicide vector. PCR is used to prove the existence of the ΔasdA16 mutation.

Figure 4:
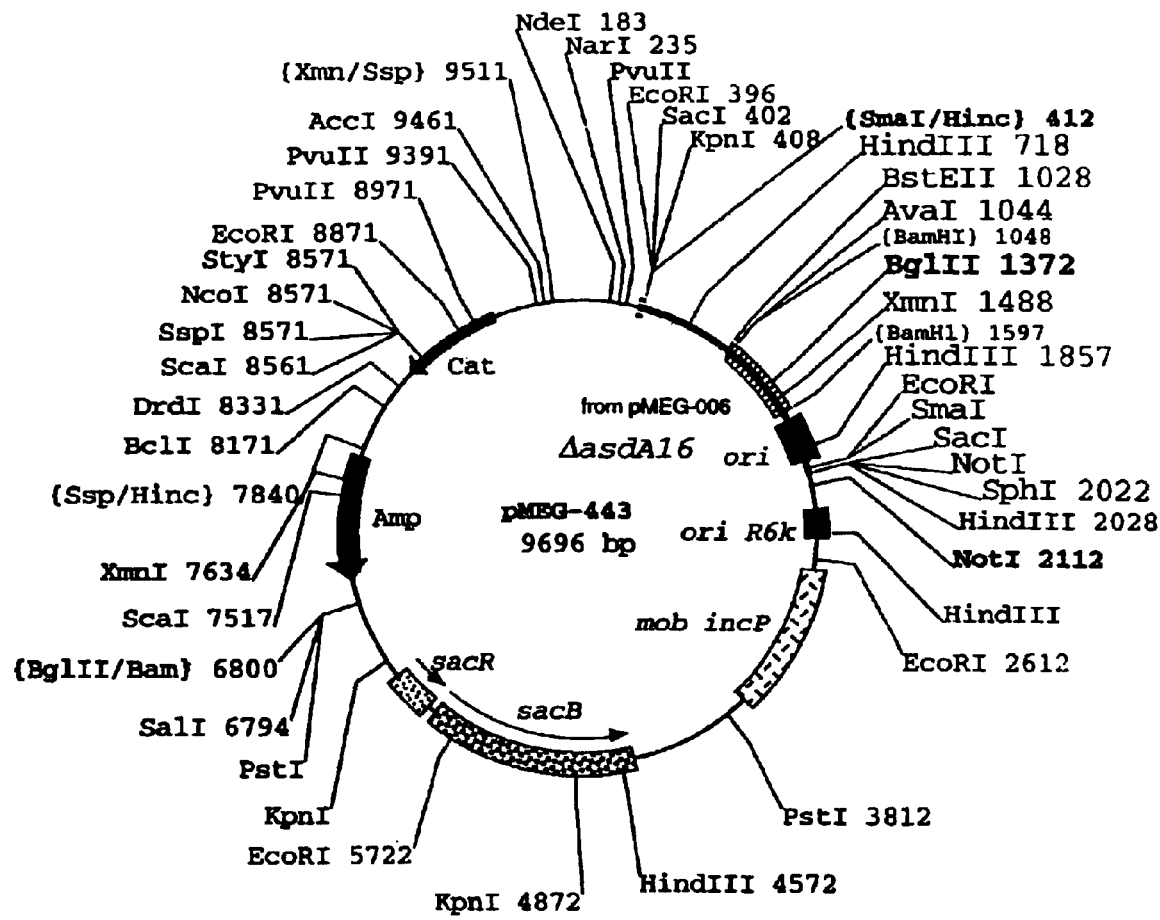
FIG. 4 illustrates the structure of pMEG-443, a pir-dependent suicide vector for allele replacement of the ΔasdA16.

Since the pMEG-006 suicide vector specifying tetracycline resistance, which necessitates fusaric acid selection to achieve allele replacement, does not always work efficiently, an additional suicide vector was constructed. This vector still has the pir-dependent R6K replicon, genes for ampicillin resistance and chloramphenicol resistance to ensure integration of the suicide vector into the chromosome of recipient strains, but has the sacR and sacB genes, conferring sensitivity to sucrose, to enable efficient selection for excision of the vector from the chromosome to achieve the second crossover event to generate the allele replacement. The vector pMEG443 depicted in FIG. 4 was generated by excising the 1.5 kb HincII-SphI fragment of pMEG-006 containing the ΔasdA16 allele along with the R6K ori and inserting it into the SmaI and SphI sites in the suicide vector pMEG-375. The pMEG-443 suicide vector was then introduced into the suicide vector donor strain MGN-617, which was then mated with the desired recipient strain. This was followed by selection for ampicillin and chloramphenicol resistance. Isolates resistant to ampicillin and chloramphenicol were purified, grown up in L broth, and then plated in the presence of 5% sucrose to select for a second crossover event, which sometimes occurs so that the ΔasdA16 mutation replaces the wild-type asd sequence within the chromosome of the recipient strain. All manipulations were conducted in the presence of DAP. The presence of the defined ΔasdA16 deletion was confirmed by PCR.

2. Generation of a Defined Deletion Mutation Within the S. typhimurium asd Gene and Replacing it with a xylE Reporter Gene Identified by a Screen with a Chromogenic Substrate.

The S. typhimurium asd gene, on a 1735 bp BglII fragment, was isolated from the cloning vector pYA292 (FIG. 16 of U.S. Pat. No. 5,672,345). This fragment was inserted into the vector pIC20H (Marsh et al., Gene 32:481485, 1984) to generate pMEG-163. An internal 725 bp EcoRV fragment from the asd gene coding region was deleted and replaced by a 957 bp BglII promoterless xylE reporter cassette from pSB383 (Kaniga et al., Mol. Microbiol. 13:555–568, 1994) so that xylE expression was driven by the asd promoter. The BglII sites of the xylE fragment were filled in using the large fragment of DNA polymerase I. Blunt-end ligation to the EcoRV sites followed, which generated pMEG-222. The defined deletion with insertion allele was initially designated asΔasd729::xylE, but has been renamed to conform with a series of asd alleles constructed by us and is now designated as ΔasdA20::xylE.

Figure 5:
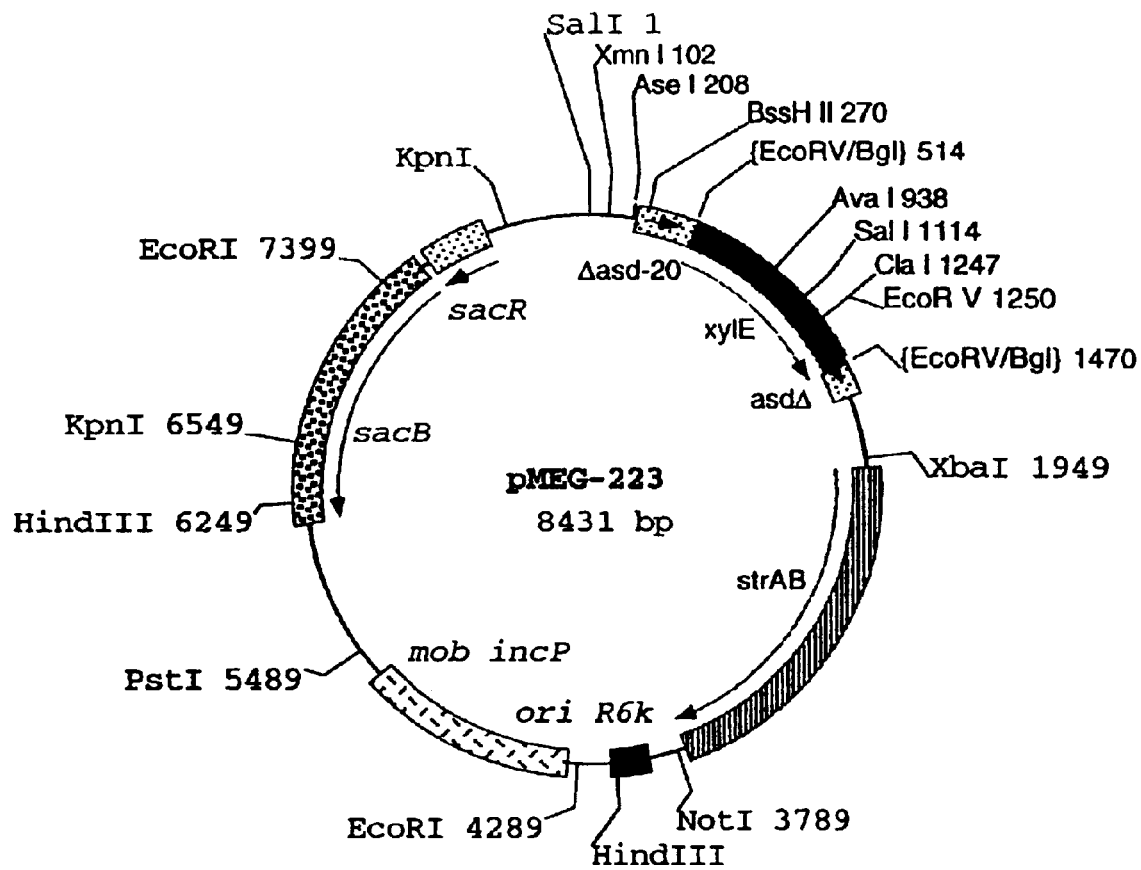
FIG. 5 illustrates the composition of pMEG-223, a pir-dependent suicide vector containing the ΔasdA20::xylE construction for transfer of that mutation to the chromosome of *Salmonella* strains.

The ΔasdA20::xylE allele and flanking sequences was retrieved from pMEG-222 as a BglII-XbaI fragment which was then inserted into the BamHI-XbaI sites of the sucrose-based suicide vector pKNG-101 (Kaniga et al., Gene 109:137–141,1991) to yield pMEG-223 which is depicted in FIG. 5. The suicide plasmid pMEG-223 was electroporated into the universal donor strain MGN-617. The ΔasdA20::xylE allele was introduced into the chromosome of several *S. typhimurium* strains including MGN-762 (ΔphoPQ23), MGN-1036 (ΔpoxA270) and into other strains as listed in Table 1. The MGN-617 donor strain with pMEG-223 was grown over night in Luria broth, as was a recipient strain, such as the prototroph $\chi$3761 (Table 1). Samples of donor and recipient over night cultures (100 μl) were introduced into 5 ml BSG, filtered through a sterile 0.45 μm Millipore filter and the filter aseptically placed on top of a Luria agar plate containing 100 μg DAP/ml. The plates were incubated at 37° C. for 8 to 17 h after which 3 to 5 ml of BSG was poured onto the plates with the filter inverted and subsequent resuspension of bacteria using a micropipette. The resuspended bacteria were serially diluted in BSG and 100 μl samples of the $10^0$, $10^{-1}$, and $10^{-2}$ dilutions were plated on selective media which was Luria agar containing 100 mg streptomycin/ml but lacking DAP (to select against growth of MGN-617). The plates were incubated at 37° C. over night with the expectation of recovering some 30 colonies per plate from the $10^{-2}$ dilution and 200 colonies or so per plate for the $10^{-1}$ dilution. After overnight incubation, the plates were sprayed with a 250 mM catechol solution and yellow colonies which appeared within 5 min were restreaked to obtain isolated colonies on Luria agar containing streptomycin. These colonies are merodiploids for the asd gene in that the suicide vector pMEG-223 with the Δasd20::xylE allele was inserted into the chromosome which still had the wild-type asd allele. Small cultures of individual colonies were prepared and plated on Luria agar containing 100 μg DAP/ml plus 5% sucrose. Sucrose-resistant colonies, indicating recombinational loss of the suicide vector, were then sprayed with 250 mM catechol solution and yellow colonies picked, restreaked, and tested for DAP requirement by streaking on media with and without DAP. XylE expressing DAP-requiring colonies were also verified to be streptomycin sensitive and sucrose resistant, both indicating loss of genes present on the suicide vector pMEG-223. The extent of the deletion and the insertion were confirmed by PCR.

Figure 6A:
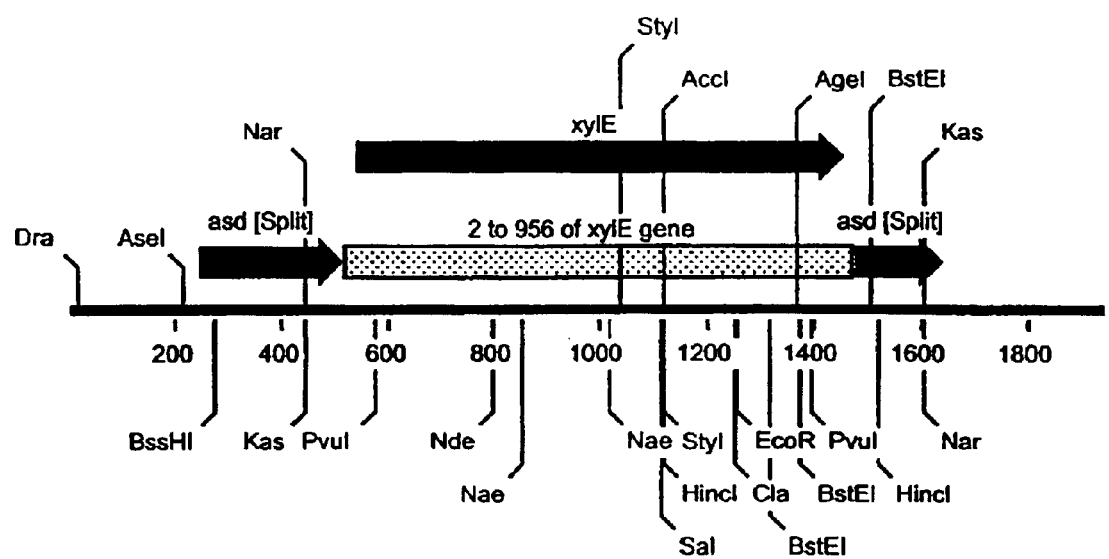
FIG. 6A is a genetic map of the ΔasdA20::xylE defined deletion/insertion, showing common restriction sites and the xylE open reading frame.

FIG. 6B specifies the nucleotide sequence of the ΔasdA20::xylE allele (SEQ ID NO:3) which includes 244 bp upstream of the asd ATG start site, an ORF containing the first 273 bp of the 5' portion of the asd gene, a 957 bp fragment containing the xylE gene which replaces a 729 bp deletion of the asd gene between the EcoRV sites, and is followed by a 174 bp region from the 3' portion of the asd ORF, and lastly the 315 bp downstream from the asd ORF.

3. Generation of Asd⁺Vectors Possessing the NcoI Initiation Cloning Site and Having Various Copy Numbers Specified by Different Plasmid Replicons.

The level of foreign proteins, especially antigens, expressed by recombinant bacteria having a Δasd mutation in the chromosome and an Asd⁺vector is dependent upon the plasmid copy number when expression is driven by the constitutive promoter $P_{trc}$. For this reason, the Asd⁺vector pYA292 (FIG. 16 of U.S. Pat. No. 5,672,345) was modified in several ways.

In one modification the multiple cloning site (MCS) in FIG. 6 of U.S. Pat. No. 5,672,345 was modified to allow insertion of native full-length sequences commencing with the ATG start codon. This was accomplished by using PCR to delete two Cs following the ATG start codon in the MCS. This generated the NcoI recognition sequence CCATGG and changed the amino acid coding sequence in the MCS downstream from the NcoI site. This modified sequence (SEQ ID NO:8) is depicted in FIG. 7.

A second modification deleted the 750 base pair HindIII fragment encoding the lacZα sequence present on pYA292 (FIG. 16 of U.S. Pat. No. 5,672,345). Originally, the lacZα sequence was used for detection of successful cloning by examining for the presence or absence of complementation as indicated by blue versus white colonies on agar medium with X-Gal. However, in many instances the lacZα fragment coding sequence was tacked on to the C-terminal end of other proteins, such that in-frame constructs would yield a blue reaction suggesting a failure when, in fact, successful cloning had been achieved. Also when the cloning event yielded out-of-frame constructs, the production of a C-terminal peptide sequence that was somewhat toxic often resulted. Since the cloning process was never a problem, the 750 base pair sequence in pYA292 was deleted to generate the plasmid pYA810.

Figure 8:
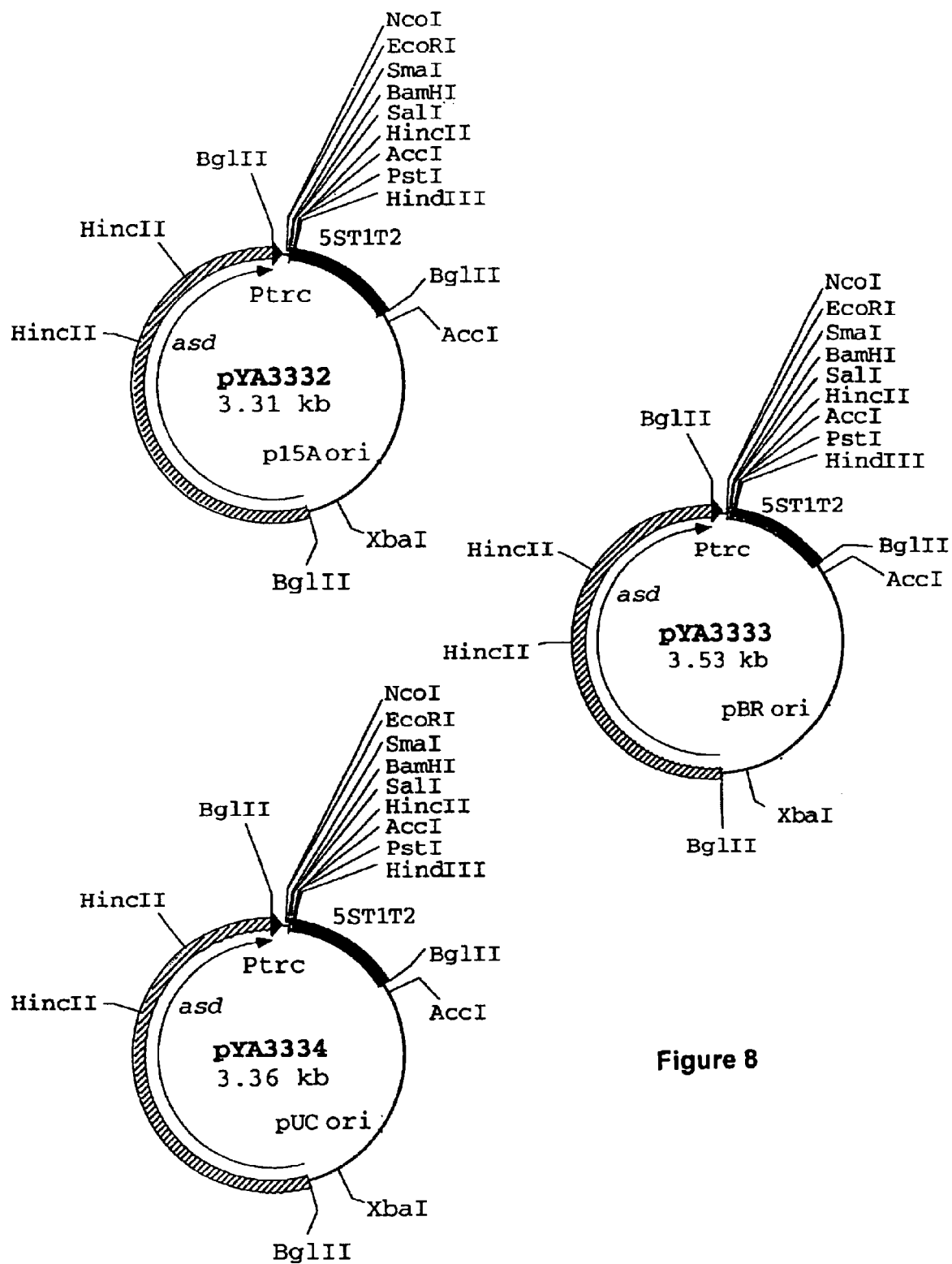
FIG. 8 illustrates the composition of Asd+cloning vectors with low, moderate and high plasmid copy numbers due to the p15A, pBR and pUC replicons, respectively, represented by pYA3332, pYA3333, and pYA3334, respectively, all of which have been engineered to possess a multiple cloning site with the NcoI restriction site to enable cloning of full-length coding sequences starting with an ATG codon.

In a third modification, a plasmid was constructed, pYA3332, which has the NcoI site and lacks the lacZα sequence but retains the p15A replicon, allowing about 20 plasmid copies per chromosome DNA equivalent. That plasmid is depicted in FIG. 8. The 830 base pair sequence between the AccI and XbaI site which contains the p15A origin of replication was replaced with the 1055 bp pBR origin of replication or the 884 bp pUC origin of replication to yield pYA3333 and pYA3334, respectively (FIG. 8). pYA3333 is present in 50 to 80 copies per chromosome DNA equivalent, whereas pYA3334 is present at 150 to 200 copies per chromosome DNA equivalent. When the same DNA sequence encoding a foreign gene product is inserted into the MCS in these three vectors and they in turn are electroporated into an *E. coli* or *S. typhimurium* Δasd mutant, the level of foreign protein synthesized is more or less proportional to the plasmid copy number with the highest level of protein expressed in the strain having the recombinant pYA3334 vector, the intermediate level produced by the strain possessing the pYA3333 vector, and the lowest level of protein produced in the strain with the pYA3332 vector.

4. Construction of Asd⁺Vectors with Reduced Expression of the asd Gene.

Studies were performed to determine whether the recombinant Asd⁺strains of the present invention exhibited wild-type virulence and were not attenuated due to overproduction of either plasmid DNA or, especially, the Asd enzyme. In this regard, the virulence of the *S. typhimurium* UK-1 strain MGN-023 with various plasmid vectors was evaluated. That strain possesses the ΔasdA16 allele as the mutated essential gene, but is able to synthesize DAP when a plasmid vector comprising a complementing asd gene is present. Here, the complementing plasmids have differing copy numbers through utilization of different origins of replication.

Strains derived from MGN-023 were therefore constructed with plasmids containing an asd complementing recombinant gene along with (a) the pSCI 01 origin of replication (pYA3074), giving a very low level of Asd enzyme synthesis; (b) the p15A origin of replication (pYA292) giving a higher level of synthesis of the Asd enzyme; (c) the pBR322 origin of replication (pYA3149), yielding a still higher level of Asd enzyme synthesis; and (d) the pUC origin of replication (pYA3137), giving the highest level of Asd enzyme synthesis. Mice were inoculated with various amounts of the recombinant bacteria as previously described, and the virulence of the bacteria was determined and an $LD_{50}$ for the various bacteria was calculated. Results of these experiments are shown in Table 3. MGN-023 with pYA3137, having the pUC origin of replication, was significantly less virulent than any of the recombinant strains of the wild-type S. typhimurium UK-1 parent, $\chi$3761. Replication studies with these strains generally found that the Asd⁺vectors with the pBR origin of replication were slightly attenuated and that Asd⁺vectors with a pUC origin were more significantly attenuated, suggesting that overproduction of the Asd enzyme is attenuating.

Therefore, the asd gene with its SD sequence but lacking the −35 and −10 components of its promoter is transcribed to yield enough asd mRNA to permit synthesis of enough Asd enzyme and DAP to retain cell viability.

In comparing E. coli and S. typhimurium strains with the plasmid vectors pYA3333 and pYA3334 (FIG. 8) and strains with plasmids pYA3342 and pYA3341 (FIG. 9), it appeared that strains with the latter two plasmids grew more rapidly than those with the plasmid vectors specifying a higher level of Asd enzyme. This growth advantage effect was relatively minor, however, and it became of interest to see whether

TABLE 3

Mortality of 8-week-old BALB/c mice 30 days after oral inoculation with S. typhimurium UK-1 strain MGN-023 (ΔasdA16) containing Asd⁺ vectors with different copy numbers.

| Strain | Genotype | Inoculating dose (DFU) | Survivors/total | MMD* | $LD_{50}$ (CFU) |
|---|---|---|---|---|---|
| χ3761 | wild-type | 1.54 × 10⁶ | 1/4 | 11.6 | 7.1 × 10⁴ |
|  |  | 1.54 × 10⁵ | 1/4 | 10.6 |  |
|  |  | 1.54 × 10⁴ | 3/4 | 10.0 |  |
|  |  | 1.54 × 10³ | 4/4 |  |  |
|  |  |  | (9/16) |  |  |
| MGN-023 | ΔasdA16 | 1.70 × 10⁶ | 0/4 | 12.7 | 4.0 × 10⁵ |
| pYA3074 | containing Asd⁺ | 1.70 × 10⁵ | 4/4 |  |  |
|  | vector with pSC101 | 1.70 × 10⁴ | 3/4 | 13.0 |  |
|  | origin | 1.70 × 10³ | 4/4 |  |  |
|  |  |  | (11/16) |  |  |
| MGN-023 | ΔasdA16 | 1.42 × 10⁶ | 2/4 | 10 | 3.3 × 10⁵ |
| pYA292 | containing Asd⁺ | 1.42 × 10⁵ | 3/4 | 16 |  |
|  | vector with p15A | 1.42 × 10⁴ | 3/4 | 20 |  |
|  | origin | 1.42 × 10³ | 3/4 | 23 |  |
|  |  |  | (11/16) |  |  |
| MGN-023 | ΔasdA16 | 1.34 × 10⁶ | 1/4 | 12 | 2.2 × 10⁴ |
| pYA3149 | containing Asd⁺ | 1.34 × 10⁵ | 0/4 | 15.7 |  |
|  | vector with | 1.34 × 10⁴ | 2/4 | 16.5 |  |
|  | pBR322 origin | 1.34 × 10³ | 4/4 |  |  |
|  |  |  | (7/16) |  |  |
| MGN-023 | ΔasdA16 | 1.54 × 10⁶ | 4/4 |  | >1.54 × 10⁶ |
| pYA3137 | containing Asd⁺ | 1.54 × 10⁵ | 4/4 |  |  |
|  | vector with pUC | 1.54 × 10⁴ | 4/4 |  |  |
|  | origin | 1.54 × 10³ | 4/4 |  |  |
|  |  |  | (16/16) |  |  |

*MDD: Mean no. days to death

Based on previous results, it is apparent that the use of pBR- and pUC-based Asd⁺vectors to induce high-level immune responses to an expressed foreign antigen might be compromised by overproduction of the Asd enzyme. Therefore, experiments were conducted to determine whether the asd coding sequence could be truncated to reduce its level of expression.

Figure 9:
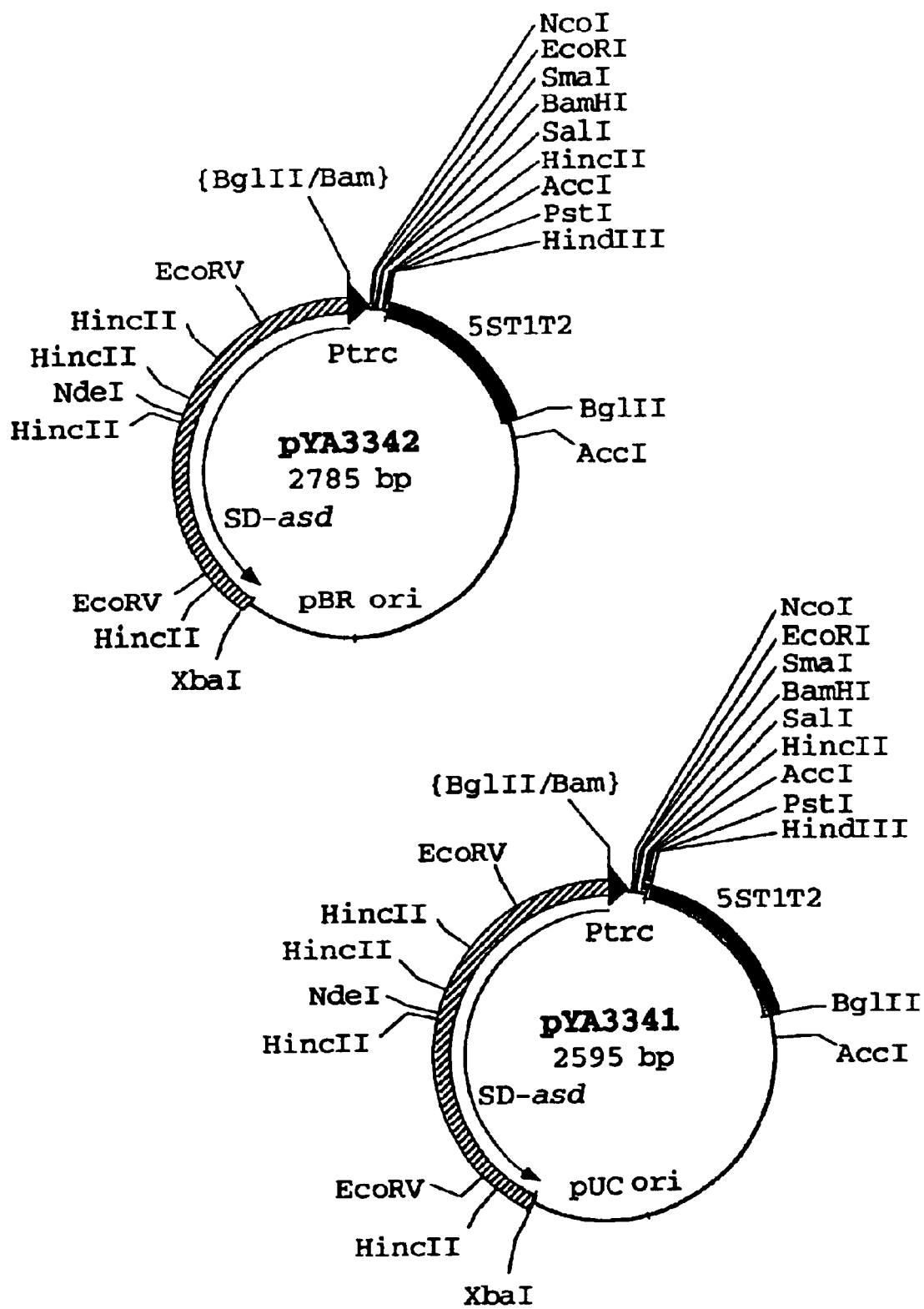
FIG. 9 depicts the moderate (pBR) and high (pUC) copy number Asd+plasmid vectors pYA3342 and pYA3341 that have been engineered to reduce the level of Asd protein expressed due to deletion of the asd gene −35 and −10 promoter sequences.

The asd gene sequence was amplified by PCR starting at base pair 286 and ending on base pair 1421 (see FIG. 2A). This sequence contains the Shine-Dalgarno (SD) sequence for ribosome recognition but lacks the RNA polymerase −35 recognition sequence and the promoter −10 sequence and ends just after the asd gene TAG stop codon with an additional terminal T. This PCR fragment was synthesized with an N-terminal BglII site and a C-terminal XbaI site. After cleavage with BglII and XbaI, the sequence was used to construct various Asd⁺vectors such as pYA3342 (pBR ori) and pYA3341 (pUC ori) (FIG. 9). After religation, the recombinant vectors were electroporated into Δasd E. coli strain $\chi$6212 to select DAP-independent recombinants. The plasmids were then reisolated from these recombinants and introduced into the ΔasdA16 S. typhimurium strain MGN-023 for selection of DAP-independent recombinants. Surprisingly, DAP-independent clones were obtained.

there was any difference in the genetic stability of strains. A procedure analogous to that described in Example 15 of U.S. Pat. No. 5,672,345 was therefore carried out. In this study, recombinant cultures were inoculated into 5 ml of Luria broth and incubated at 37° C. overnight. The next morning the cultures were diluted 1:1000 into 5 ml of prewarmed Luria broth and the procedure repeated daily for at least five days. Since each 1:1000 dilution constitutes ten generations of growth, a total of 50 or 60 generations of growth were permitted for cells grown either in the presence or absence of DAP. For all strains with all Asd⁺plasmids 100% of over 100 colonies tested for each strain after 10, 20, 30, 40, and 50 generations of growth remained Asd⁺and contained plasmid DNA.

Another important parameter to evaluate is whether the amount of Asd enzyme was significantly reduced in strains possessing pYA3342 and pYA3341 compared to strains with plasmids pYA3333 and pYA3334 that had asd genes with the asd promoter. FIG. 10 presents the results of an experiment in which strains were grown in Luria broth and a constant amount of protein was loaded on a polyacrylamide gel and electrophoresed after which a Coomassie brilliant blue stain was used to identify protein bands. As is readily seen, protein bands having the size of the Asd protein (39 kDa) are readily apparent in bacteria having Asd⁺plasmids with the asd promoter and are not readily detectable in protein extracts from cells harboring the pYA3342 and pYA3341 plasmids with the SD-asd sequence lacking the asd promoter. These results thus explain the better growth of strains having the plasmids with the SD-asd sequence and also warrants their use in vaccine compositions since there would be less competition for the protein synthesis machinery and more could be devoted to synthesizing a foreign protein, especially an antigen, encoded by a sequence cloned into the Asd⁺vector multiple cloning site. It should be apparent from these considerations that decreasing the level of Asd protein synthesis also reduces the selective pressure against maintenance of the plasmid and thus should enhance the utility of strains harboring these plasmid vectors for any of their intended uses. In this regard, S. typhimurium UK-1 MGN-023 with the ΔasdA16 mutation could be restored to wild-type virulence by introducing either pYA3342 or pYA3341, results that justify the advantage of reducing the level of Asd enzyme synthesized by strains with Asd⁺ vectors.

Although E. coli and S. typhimurium strains with a Δasd mutation and possessing the plasmids pYA3342 or pYA3341, each with the SD-asd sequence, grow at the same rate in medium with or without DAP, it is apparent that such cells transcribe, by some unknown mechanism, a sufficient amount of mRNA to cause synthesis of a sufficient amount of Asd protein to carry out the biosynthetic pathway to synthesize DAP. That is, they synthesize enough DAP so that DAP is not limiting for growth. However, numerous attempts to subclone the BglII-XbaI fragment containing the SD-asd sequence into plasmid vectors with either the p15A replicon or the pSC101 replicon, which has an even lower copy number than the p15A replicon, were unsuccessful. It is therefore apparent that in these cases there is an insufficient number of copies of the plasmid DNA so that chance transcription would synthesize a sufficient amount of mRNA to cause synthesis of enough Asd enzyme to support growth in the absence of exogenously supplied DAP. This hypothesis was confirmed by the ability to make such constructs and introduce them into cells provided that DAP was contained in the medium. In all cases, removal of DAP from the growth medium led to the inability of the recombinant cells to grow and survive.

As would be understood by the skilled artisan, the above-described scheme of retaining the SD sequence but eliminating the −35 polymerase recognition sequence and the promoter −10 sequence would also be useful for other selective markers when a high copy number plasmid is used, for example when high levels of expression of a desired gene is useful, but where the concurrent excessive expression of the selective marker is disadvantageous. Non-limiting examples of other selective markers useful in these embodiments are drug resistance markers, purA⁺, purB⁺, thyA⁺, and trp⁺.

5. Complementation and Possibilities of Recombination Between Asd⁺Vectors and Chromosome with Δasd Mutations.

Figure 11:
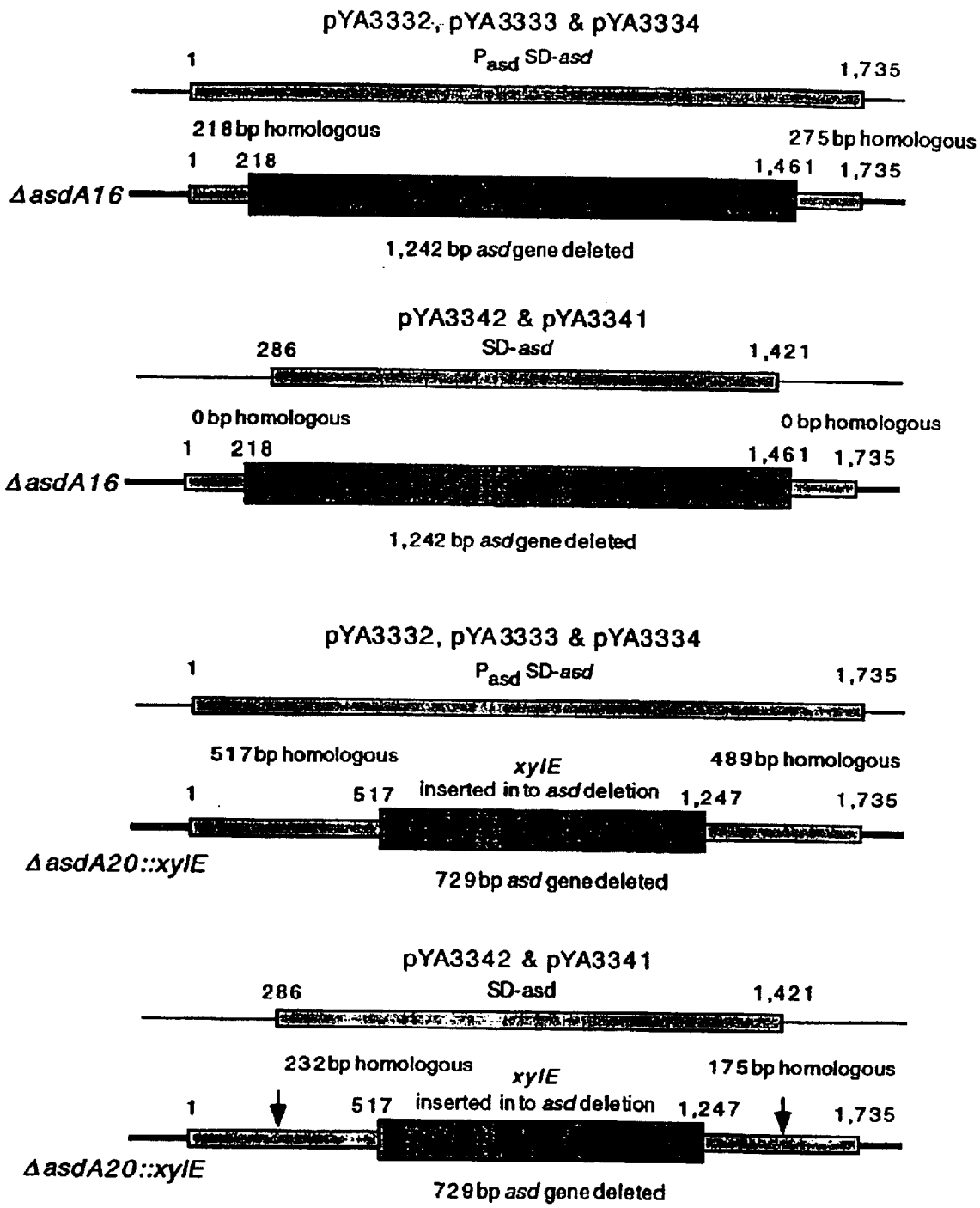
FIG. 11 represents an illustration of the extent of sequences encoding the wild-type asd gene and its 5' and 3' flanking sequences as found on various Asd⁺vectors and the extent of deletions with or without the xylE insertion in the chromosome of constructed *S. typhimurium* strains to depict in a scale model the possible regions in which recombination between homologous sequences on the vector and the chromosome might occur.

With transposon-induced Δasd mutations, much or all of the asd gene was deleted, but importantly also DNA sequences flanking the asd gene such that it was always impossible to have a double crossover event between the wild-type asd sequence on any of the Asd⁺plasmid vectors constructed and the chromosome to result in restoration of the chromosome to an asd⁺genotype. This is because one of the recombination events must be on one side of the chromosomal deletion mutation encompassing the asd gene and the other must be on the other side of this deletion mutation. As depicted in FIGS. 11, the ΔasdA16 chromosomal mutation deletes bp 219 to 1460 inclusive of the DNA sequence encoding asd and its 5' and 3' flanking regions (FIG. 2A). The pYA3332, pYA3333, and pYA3334 Asd⁺vectors have the entire 1735 base pair sequence, thus having 218 bp of homology 5' to the Δasd416 mutation and 275 bp 3' to the Δasd416 deletion. Thus, it is possible that double homologous recombination events could occur to enable the Asd⁺ sequence present in these Asd⁺vectors to recombine with the chromosome to eliminate the Δasd 16 mutation and replace it with the vector wild-type Asd⁺sequence. In contrast, the plasmids pYA3342 and pYA3341 only contain the SD-asd sequence going from 286 bp to 1421 bp (FIG. 2A) and there is no nucleotide sequence homology remaining in those vectors with the chromosome remaining in strains that have the ΔasdA16 mutation. This is readily seen by examination of the top portion of FIG. 11. Although we have seen complete stability in maintenance of Asd⁺plasmids with or without recombinant foreign gene inserts encoding proteins, especially antigens, in strains possessing the ΔasdA16 mutation, it is desirable to determine whether the balanced-lethal host-vector systems comprising nucleotide sequence homology between sequences on the vector and sequences in the chromosome (enabling double crossover events to occur) did in fact impair the utility of the balanced-lethal host-vector systems. In order to evaluate this, it was critically important to be able to recognize with a high degree of precision and with ability to detect very rare events the potential loss of the Δasdmutation in the chromosome. For this reason, the ΔasdA20::xylE construction was made since cells harboring this deletion mutation with or without an Asd⁺plasmid become yellow following spray with catechol. As can be seen in the bottom portion of FIG. 11, plasmids such as pYA3332, pYA3333, and pYA3334 possess regions of DNA sequence homology, both 5' and 3' to the internal deletion of 729 bp of the asd gene and the xylE coding sequence. Thus the plasmids pYA3332, pYA3333, and pYA3334 possess 517 bp of homology 5' to the deletion and 499 bp 3' to the deletion. In these cases the lengths of homologous sequences are longer than when these same Asd⁺plasmids are present in bacterial strains with the ΔasdA16 mutation. Also, there is homology between the SD-asd sequence on pYA3342 and pYA3341 and sequences 5' and 3' to the asdA20::xylE mutation in the chromosome. In this case, there is 232 bp 5' to the deletion and 175 bp 3' to the deletion, thus making double crossover recombination theoretically possible so as to replace the chromosomal ΔasdA20::xylE mutant allele with the wild-type SD-asd⁺ sequence on the Asd⁺plasmids.

To evaluate the stability of plasmid constructs in Salmonella strains with defined deletions of the asd gene we explored the stability after repetitive growth cycles in the presence of DAP in vitro and then investigated for stability after immunization of female BALB/c mice with recombinant constructs. For the in vitro evaluations, we therefore constructed recombinants by introducing the pBR based replicon pYA3342 possessing the SD-asd sequence into X315 (ΔphoPQ23 ΔasdA20::xylE) and into χ8316 (ΔpoxA270 Δasd420::xylE). Overnight cultures in Luria broth of the recombinant constructs were diluted 1:1000 (5 μl into 5 ml) in prewarmed Luria broth containing 50 μg DAP/ml and grown without aeration at 37° C. for 16 h. The next day the cultures were diluted and plated on L agar plus DAP and incubated at 37° C. One hundred colonies of each of the strains were picked and inoculated onto L agar with or without DAP to determine loss of the vector. Colonies grown on L agar without DAP were considered Asd$^+$. After incubation, colonies were sprayed with 250 mM catechol to determine loss of the xylE marker. Yellow colonies were considered XylE$^+$. The process was repeated daily for five days until the culture had grown to the 50th generation. The results are presented in Table 4, and indicate that all 100 colonies from both strains after 10, 20, 30, 40, and 50 generations of growth were phenotypically Asd$^+$and XylE$^+$. In addition, six colonies of each strain were picked and grown up with DAP and the presence of the plasmid was examined; all 30 isolates of both strains contained pYA3342. Thus even though double crossover recombination between the sequence in pYA3342 and the sequences flanking the xylE insert in the ΔasdA20::xylE mutation were possible, no such recombinations occurred at detectable frequencies.

TABLE 4

In vitro stability of xylE marker in χ8315 (ΔphoPQ23 ΔasdA20::xylE) (pYA3342) and χ8316 (ΔpoxA270 ΔasdA20::xylE)(pYA3342) in Luria broth plus DAP

| Strains | Number of Asd$^+$ XylE$^+$ colonies/100 colonies tested* | | | | |
|---|---|---|---|---|---|
| | 10 Gen | 20 Gen | 30 Gen | 40 Gen | 50 Gen |
| χ8315(pYA3342) | 100 | 100 | 100 | 100 | 100 |
| χ8316(pYA3342) | 100 | 100 | 100 | 100 | 100 |

*No Asd$^+$ XylE$^-$ colonies were observed.

A more permissive test was conducted by introducing the pBR based plasmid pYA3333 into χ8315 and χ8316 since the regions of DNA sequence homology to enable double crossover event is more extensive (see FIG. 11, bottom). The experiment to evaluate in vitro stability was repeated exactly as had been done for the strains possessing pYA3342. In this case, all 100 colonies from both strains after 10, 20, 30, 40 and 50 generations of growth were phenotypically Asd$^+$and XylE$^+$and of the 6 colonies of each strain evaluated after each growth cycle all possessed the plasmid pYA3333. Thus even though double crossover recombination is more likely in these constructs because of the more substantial amount of DNA sequence homology flanking the xylE insertion into the ΔasdA20 allele in the chromosome, no such double crossover events were detected.

Even greater selective pressure was applied by introducing recombinant strains by oral inoculation into mice a nd evaluating recovered microorganisms for the relevant phenotypes. For these experiments the bacteria strains were grown over night in static cultures in Luria broth. The next day, cultures were diluted 1:1100 into prewarmed Luria broth and grown with aeration by shaking until an OD 600 of 0.85 was reached. The cultures were sedimented by centrifugation at room temperature using the SS3A rotor at 6500 rpm for 20 min. Bacterial cells were resuspended in BSG to a proper concentration and titration by dilution was performed to assess the CFUs/ml in the concentrated suspensions. Eight week old female BALB/c mice that had been acclimated in our animal facility for one week prior to use were inoculated orally with 20 μl containing 10$^9$ CFU of the bacterial strain. Five mice were used for each of the four strains evaluated. Peyer's patches and spleens of all mice were taken at seven and ten days after oral inoculation. Tissues were homogenized and plated on MacConkey agar containing 1% lactose and 50 μg DAP/ml. One hundred colonies from each of the strains were picked onto L agar with or without DAP, incubated, and sprayed with 250 mM catechol solution. As indicated by the data in Table 5, all 200 isolates of either χ8315 containing pYA3342 or χ8316 containing pYA3342 remained Asd$^+$and XylE$^+$. None of these isolates were Asd$^{+\ and\ XylE-}$ and all bacteria tested still contained the pYA3342 Asd$^+$vector. In the experiment with χ8315 and χ8316 possessing the asd vector pYA3333 we observed total stability in bacteria recovered seven days after oral inoculation, with all bacteria being Asd$^+$ and XylE$^+$ and all tested isolates still possessed the Asd$^+$ plasmid pYA$^{3333}$ (Table 6). On the other hand, 8 of 93 isolates obtained 10 days following oral inoculation of mice with χ8315 containing pYA3333 had lost the chromosomal asd mutation with the xylE insertion but remained Asd$^+$ because of replacement of the chromosomal mutant allele by double crossover recombination. No such isolates were observed 10 days after oral inoculation with the ΔpoxA270 strain χ8316 (Table 6).

TABLE 5

In vivo stability of xylE marker in χ8315 (ΔphoPQ23 ΔasdA20::xylE) (pYA3342) and χ8316 (ΔpoxA270 ΔasdA20::xylE)(pYA3342) in mice*.

| Strains | Asd$^+$ | Asd$^+$XylE$^+$ | Asd$^+$XylE$^-$ |
|---|---|---|---|
| χ8315(pYA3342) | 200/200 | 200/200 | 0/200 |
| χ8316(pYA3342) | 200/200 | 200/200 | 0/200 |

*Bacteria were isolated from internal lymphoid organs of mice on day 10 after oral inoculation with 109 CFU and plated on MacConkey agar + Lactose + DAP and replica plated onto L agar with or without DAP and then sprayed with 250 mM catechol solution.

TABLE 6

Frequency of loss of Asd$^+$ vector and/or xylE marker in χ8315 (ΔphoPQ23 ΔasdA20::xylE)(pYA3333) and χ8316 (ΔpoxA270 ΔasdA20::xylE) (pYA3333) in mice*.

| Days | Strains | Asd$^+$ | Asd$^+$XylE$^+$ | Asd$^+$XylE$^-$ |
|---|---|---|---|---|
| 7 | χ8315(pYA3333) | 100/100 | 100/100 | 0/100 |
| 10 | χ8315(pYA3333) | 93/93 | 85/93 | 8/93 |
| 7 | χ8316(pYA3333) | 100/100 | 100/100 | 0/100 |
| 10 | χ8316(pYA3333) | 100/100 | 100/100 | 0/100 |

*Bacteria were isolated from internal lymphoid organs of mice on days 7 and 10 after oral inoculation and plated on MacConkey agar + Lactose + DAP and replica plated onto L agar with or without DAP and then sprayed with 250 mM catechol solution.

Taken collectively, the experiments of recovering microorganisms following oral inoculation of mice revealed that the theoretical possibility of recombination can occur with very low frequency after numerous generations of growth under highly selective in vivo conditions, at least in one of the two instances studied.

It is apparent from these results that the theoretical possibility of recombination does not mandate that such recombination does indeed occur or occurs at frequencies that would compromise the use of these balanced-lethal host-vector systems. In this regard, it should be recalled that use of recombinant attenuated *S. typhimurium* vaccine strains that had plasmid vectors encoding a foreign antigen and which were maintained in vitro by growth in the presence of antibiotics to which the plasmid vector conferred resistance, often led to no more than 10 percent of the *Salmonella* cells recovered as soon as three days after oral inoculation of mice retaining the plasmid vector and expressing the foreign antigen (see Nakayama et al., 1988; Curtiss et al., Curr. Top. Microbiol. Immun.146:35–49, 1989).

There are several possible explanations for the functional stability of the recombinant strains described in this Example. First, transient integration of the plasmid into the chromosome, even if followed soon thereafter by a second recombination event excising the plasmid from the chromosome, may be inhibited when there are multiple copies of plasmid DNA in the cytoplasm of the bacterial cells. It is well known that plasmids capable of integration do so and then generally preclude the maintenance of plasmids in the cytoplasm and similarly, plasmids existing in the cytoplasm seem to interfere with the common presence of the plasmid sequence in the chromosome. This is best understood from studies in the 1950s and 1960s on the inability of the F plasmid to be stably maintained in Hfr cells that possess the same F plasmid integrated into their chromosome. In $F^+$ cells with F in the cytoplasm, rare F integration events occur in which F replicates under control of chromosome replication with the consequence that the cytoplasmic F disappears. Similarly, it is well known that λ lysogens with λ prophage integrated into the chromosome fail to support lambda replication in the cytoplasm. Thus, co-existence of cytoplasmic and integrated states of $Asd^+$ vectors, even though transient, may be inhibited from occurrence. A second factor possibly contributing to the rarity of a double crossover event which would be necessary for allele exchange with the wild-type plasmid asd$^+$allele replacing the chromosomal mutation is the phenomenon of positive interference, well known in the genetics of *Drosophila* and maize but also studied and recognized to occur in bacteria such as *E. coli* (Curtiss, J. Bacteriol. 89:28–40, 1965). In this case, the deletion of sequences in the chromosome necessitates that the wild-type sequence has to undergo a convolution to allow for effective homologous pairing between regions of homology on either side of the deleted sequence in the chromosome. Such effective homologous pairing is an essential first step preparatory to the recombination event. Such contortions reduce the likelihood of a second recombination event following a first event, so-called positive interference. It is also possible, of course, that the introduction of the xylE marker which is totally non-homologous to any sequence in the Asd$^+$vectors, also serves to cause positive interference and reduce the likelihood of double crossover events even though DNA sequence homology exists. Whatever the explanation, it is clear that the existence of some DNA sequence homology on either side of a deletion in the chromosome with sequences on the Asd$^+$vector does not interfere with the functional integrity of the balanced-lethal host-vector system over a number of generations either in vitro or following inoculation into an animal. The recombinant constructs illustrated in these Examples which possess such DNA sequence homologies can more than adequately perform the tasks that they are designed to do whether it be to immunize an animal host against an expressed foreign antigen or to produce a protein that has some other biological beneficial attribute.

6. DNA Vaccines Produced and/or Delivered by Bacteria Comprising a Functional Balanced-Lethal Host-Vector System.

Figure 12:
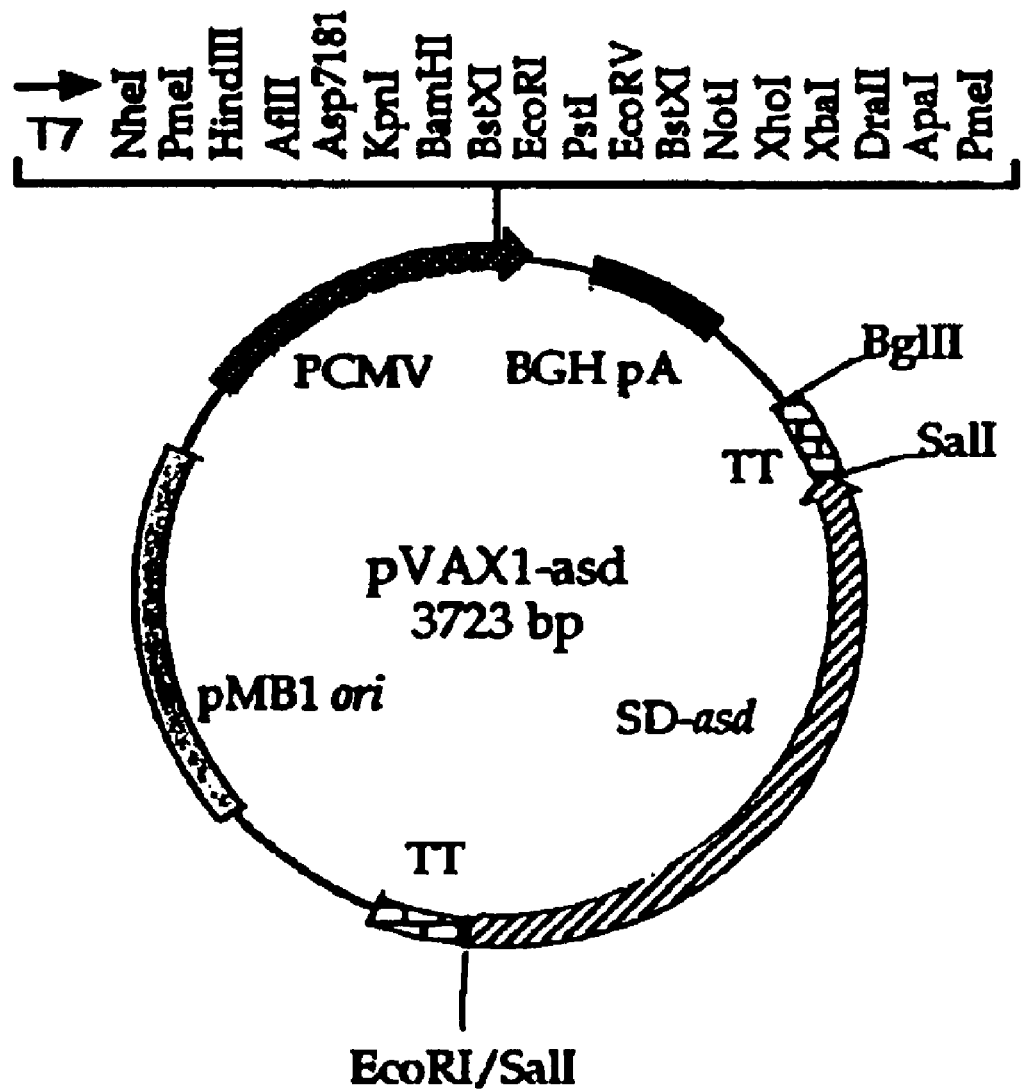
FIG. 12 depicts the composition of a high-copy number Asd⁺vector with the SD-asd sequence and designed with eukaryotic expression elements to be used for construction of DNA vaccine vectors that could be harbored and produced in bacterial strains with a Δasd mutation or delivered directly to the immunized host by attenuated bacterial strains also possessing a Δasd mutation.

DNA vaccines for immunization of individuals by direct inoculation of plasmid DNA molecules encoding the antigens from viruses, parasites, bacteria, or fungi for synthesis within and by the immunized eukaryotic host is receiving significant attention with some very encouraging results from numerous studies. See, e.g., Ulmer et al (1996a); Ulmer et al (1996b); Whalen (1996); Robinson (1997). Most of the DNA vaccine vectors possess either a kanamycin-resistance determinant or an ampicillin-resistance gene to enable maintenance of the plasmid constructs in *E. coli* strains by growth in the presence of kanamycin or ampicillin. As stated above, the addition of kanamycin or ampicillin is an expense during fermentation to produce quantities of DNA vaccine vector to use for immunization. In addition kanamycin or ampicillin must be completely removed prior to use of the DNA plasmids for immunization. Lastly, there is concern about the introduction of antibiotic resistant genes into individuals whether stably inheriting that genetic information or not. It is also known that the presence of CpG sequences that remain unmethylated in bacterial DNA when introduced into eukaryotic cells, especially antigen processing and presenting cells such as macrophages, augment the immune response to expressed foreign antigens in a significant way (see, e.g., Krieg et al., 1998, for a review). Unfortunately, the DNA sequence encoding kanamycin resistance lacks the types of CpG sequences that maximize the enhancement of the immune response. On the other hand, the asd$^+$ gene of *S. typhimurium* possesses two such sequences. It is therefore possible to construct derivatives of eukaryotic DNA vaccine vectors such as pVAX-1 by substituting the kanamycin resistance gene with the *S. typhimurium* asd gene. If a high copy number pUC vector is used, the asd sequence can be the SD-asd sequence lacking the promoter so that the amount of Asd enzyme is diminished to a level necessary to support growth and constitute a balanced-lethal host-vector system but not to result in any selective pressure that would lead to a lower plasmid copy number or poor growth properties of the recombinant constructs. Such a pVAX asd vector is diagrammed in FIG. 12. Such a vector can also be directly delivered by an attenuated bacterial DNA vaccine delivery host to immunize vertebrates against antigens specified by plasmid encoded genes. In these plasmids, expression of the antigen is controlled by (i.e., operably linked to) a eukaryotic promoter. A preferred promoter for this purpose is an immediate-early promoter from a cytomegalovirus ("a CMV promoter"), as in the vector depicted in FIG. 12. For reviews of bacterial delivery of DNA vaccines, see, e.g., Detrich et al. (1999); Detrich et al. (2000).

7. Use of Nucleotide Sequence Information for dapA, dapB, dapD, dapE, and dapF Genes to Construct and Evaluate Functional Balanced-lethal Host-vector Systems.

The nucleotide sequences for the dapA, dapB, dapD, dapE and dapF genes of *E. coli* and *S. typhimurium* are now known. See Table 7. This information can be used to generate defined deletion mutations and introduce them into the chromosome, as described in Example 1 for the asd gene, to construct defined deletion mutations with a reporter gene such as xylE as a described in Example 2, to insert these into plasmid vectors with suitable multiple cloning sites and absence of extraneous coding sequences as illustrated in Example 3, to diminish the level of expression of the DapA, DapB, DapD, DapE or DapF enzymes to an amount necessary for growth in the absence of DAP but without constituting an energy burden on cells as described in Example 4, to evaluate the functional utility and stability in vitro and in vivo of these balanced-lethal host-vector constructs as described in Example 5, and to generate DNA vaccine vectors possessing the dapA, dapB, dapD, dapE, or dapF sequences as described for the asd gene in Example 6. Other manipulations described herein for asd could also be adapted by the skilled artisan to the use of the dapA, dapB, dapD, dapE, or dapF sequences.

TABLE 7

Genbank sequences encoding DapA, DapB, DapD, DapE and DapF.

| | Salmonella typhimurium (Washington University) | | Salmonella typhi | |
|---|---|---|---|---|
| | Contig. | Corresponding segment | Contig. | Corresponding segment |
| dapA (Dihydrodipicolinate synthetase) | 295 | 786–1295 | 9 | 82379–83254 |
| dapB (Dihydrodipicolinate reductase) | 1123 | 8–505 | 1693 | 14904–15722 |
| dapD (Succinyl-diaminopimelate aminotransferase | 3548 | 1–78 | 1693 | 188012–187191 |
| dapE (N-succinyl-diaminopimelate) | 50 | 228–515 | 9 | 89605–88481 |
| dapF (Diaminopimelate epimerase) | 436 | 47869–47045 | 1694 | 43662–42838 |

INDUSTRIAL APPLICABILITY

The present invention discloses microbial cells that have an inactivating mutation in a native essential gene encoding an essential enzyme that catalyzes a step in the biosynthesis of DAP. The cells also comprise extrachromosomal vectors comprising (a) a recombinant gene which complements the inactivated native essential gene, and (b) a desired gene, encoding a desired gene product. These cells are particularly useful in (1) methods for immunization of a vertebrate, where the microbial cells are live vaccine components, and where the desired gene encodes an antigen to which immunity is induced, or an allergen to which the vertebrate is to be desensitized, or sperm-specific and egg-specific autoantigens to arrest fertility, or specific antibodies, e.g., which bind to tumors or pathogens such as viruses, fungi, parasites, or bacteria, or gene products essential for a pathogen to cause disease), or enzymes that have the potential to convert prodrugs into toxic drugs within a tumor cell mass in an individual with a solid tumor; and (2) methods for delivering a desired gene product to a vertebrate, where the desired gene encodes, for example an immunomodulatory therapeutic desired gene product such as a lymphokine or cytokine; and other purposes which would be known to the skilled artisan. Methods are also provided for producing improved DNA vaccines.

All references cited in this specification are hereby incorporated in their entirety by reference. The discussion of the references herein is intended merely to summarize the assertions made by their authors and no admission is made that any reference constitutes prior art. Applicant reserves the right to challenge the accuracy and pertinence of the cited references.

I claim:

1. An attenuated derivative of a pathogenic microorganism which comprises:
   (a) a non-functional native chromosomal essential gene;
   (b) a recombinant complementing gene on an extrachromosomal vector, wherein the complementing gene can recombine to replace the non-functional native chromosomal essential gene; and
   (c) a desired gene on the extrachromosomal vector, wherein the desired gene is a recombinant gene encoding a desired gene product;
   wherein said complementing gene of (b) is a functional replacement for said essential gene of (a), wherein the desired gene is stably maintained in a progeny population of the microorganism.

2. The microorganism of claim 1, wherein the microorganism is a member of the *Enterobacteriaceae* and the extrachromosomal vector is a plasmid.

3. The microorganism of claim 2, further comprising an inactivating mutation in a gene selected from the group consisting of a pab gene, a pur gene, an aro gene, nadA, pncB, galE, pmi, fur, rpsL, ompR, htrA, hemA, cdt, cya, crp, dam, phoP, phoQ, rfc, poxA, galU, mvlA, sodC, recA, ssrA, sirA, inv, hilA, rpoE, flgM, tonB, and slyA.

4. The microorganism of claim 3, wherein the desired gene product is an antigen.

5. The microorganism of claim 4, wherein the antigen is selected from the group consisting of a bacterial antigen, a viral antigen, a fungal antigen, a parasitic antigen, a gamete-specific antigen, an allergen, and a tumor antigen.

6. The microorganism of claim 2, wherein the essential gene is selected from the group consisting of dapA, dapB, depD, depE, dapF, and asd.

7. The microorganism of claim 6, wherein the non-functional native chromosomal essential gene is an asd gene wherein said asd gene comprises an insertion or a deletion.

8. The microorganism of claim 2, wherein the recombinant complementing gene lacks an RNA polymerase −35 recognition sequence and a promoter −10 sequence.

9. The microorganism of claim 8, wherein the recombinant complementing gene is an asd gene.

10. The microorganism of claim 2, wherein the desired gene is operably linked to a eukaryotic promoter.

11. The microorganism of claim 10, wherein the eukaryotic promoter is a CMV (cytomegalovirus) promoter.

12. A recombinant vector comprising a recombinant complementing gene, wherein the recombinant complementing gene lacks an RNA polymerase −35 recognition sequence and a promoter −10 sequence, wherein the recombinant complementing gene is a functional replacement for a non-functional native chromosomal essential gene when the vector is present in a microorganism having a non-functional native chromosomal essential gene.

13. The recombinant vector of claim 12, wherein the vector is a plasmid capable of expressing the recombinant complementing gene in a microorganism that is a member of the *Enterobacteriaceae*.

14. The recombinant vector of claim 12, wherein the recombinant complementing gene encodes an enzyme that catelyzes a step in the biosynthesis of DAP (mesodiaminopimellc acid).

15. The recombinant vector of claim 14, wherein the recombinant complementing gene is an asd gene.

16. The recombinant vector of claim 12, further comprising a gene encoding a desired gene product.

17. The recombinant vector of claim 16, wherein the desired gene product is an antigen.

18. The recombinant vector of claim 17, wherein the antigen is selected from the group consisting of a bacterial antigen, a viral antigen, a fungal antigen, a parasitic antigen, a gamete-specific antigen, an allergen, and a tumor antigen.

19. The recombinant vector of claim 16, wherein the desired gene product is therapeutic to a vertebrate.

20. The recombinant vector of claim 19, wherein the desired gene product is selected from the group consisting of a lymphokine, a cytokine, and a sperm-specific or egg-specific autoantigen.

21. The recombinant vector of claim 16, wherein the desired gene product is operably linked to a eukaryotic promoter.

22. The recombinant vector of claim 21, wherein the eukaryotic promoter is a CMV promoter.

23. An attenuated derivative of a pathogenic microorganism which comprises:
   (a) a mutation of a polynucleotide sequence that renders a native chromosomal essential gene non-functional;
   (b) a recombinant complementing gene on an extrachromosomal vector, wherein the complementing gene is functional replacement for said essential gene of (a) and wherein said complementing gene can recombine to replace the essential gene of (a); and
   (c) a desired gene on the extrachromosomal vector, wherein the desired gene is a recombinant gene encoding a desired gene product;
   wherein the desired gene is stably maintained in a progeny population of the microorganism.

24. An attenuated derivative of a pathogenic microorganism which comprises:
   (a) a non-functional native chromosomal essential gene;
   (b) a recombinant complementing gene on an extrachromosomal vector, wherein the complementing gene can recombine to replace the non-functional chromosomal essential gene;

(c) a desired gene on the extrachromosomal vector, wherein the desired gene is a recombinant gene encoding a desired gene product; and (d) an inactivating mutation in a native gene selected from the group consisting of a pab gene, a pur gene, and ar gene, nadA, pncB, gale, pmi, fur, rpsL, ompR, htrA, hemA, cdt, cya, crp, dam, phoP, phoQ, rfc, poxA, falU, mviA, sodC, recA, ssrA, sirA, inv, hilA, rpoE, flgM, tonB, and slyA;

wherein said complementing gene of (b) is a functional replacement for herein the desired gene is stably maintained in a progeny population of the microorganism.

* * * * *

SEQUENCE LISTING

```
<160> NUMBER OF SEQ ID NOS: 8

<210> SEQ ID NO 1
<211> LENGTH: 1735
<212> TYPE: DNA
<213> ORGANISM: Salmonella typhimurium

<400> SEQUENCE: 1
ggatcttccc taaatttaaa tataaacaac gaattatctc cttaacgtac gttttcgttc        60
cattggccct caaacccta attaggatca ataaaacagc gacggaaatg attcccttcc       120
taacgcaaat tccctgataa tcgccactgg actttctgct tgcgcggtaa ggcaggataa       180
gtcgcattac tgatggcttc gctatcattg attaatttca cttgcgactt tggctgcttt       240
ttgtatggtg aaggatgcgc cacaggatac tggcgcgcat acacagcaca tctctttgca       300 ggaaaaaac gctatgaaaa atgttggttt tatcggctgg cgcggaatgg tcggctctgt       360
tctcatgcaa cgcatggtag aggagcgcga tttcgacgct attcgccctg ttttcttttc       420
tacctcccag tttggacagg cggcgcccac cttcggcgac acctccaccg gcacgctaca       480
ggacgctttt gatctggatg cgctaaaagc gctcgatatc atcgtgacct gccagggcgg       540
cgattatacc aacgaaattt atccaaagct gcgcgaaagc ggatggcagg gttactggat       600
tgatgcggct tctacgctgc gcatgaaaga tgatgccatt attattctcg acccggtcaa       660
ccaggacgtg attaccgacg gcctgaacaa tggcgtgaag acctttgtgg gcggtaactg       720
taccgttagc ctgatgttga tgtcgctggg cggtctcttt gcccataatc tcgttgactg       780
ggtatccgtc gcgacctatc aggccgcctc cggcggcggc gcgcgccata tgcgcgagct       840
gttaacccag atgggtcagt tgtatggcca tgtcgccgat gaactggcga cgccgtcttc       900
```

-continued

```
cgcaattctt gatattgaac gcaaagttac ggcattgacc cgcagcggcg agctgccggt    960
tgataacttt ggcgtaccgc tggcgggaag cctgatcccc tggatcgaca acagctcga   1020
taacggccag agccgcgaag agtggaaagg ccaggcggaa accaacaaga ttctcaatac   1080
tgcctctgtg attccggttg atggtttgtg tgtgcgcgtc ggcgcgctgc gctgtcacag   1140
ccaggcgttc accatcaagc tgaaaaaaga ggtatccatt ccgacggtgg aagaactgct   1200
ggcggcacat aatccgtggg cgaaagtggt gccgaacgat cgtgatatca ctatgcgcga   1260
attaaccccg gcggcggtga ccggcacgtt gactacgccg gttggtcgtc tgcgtaagct   1320
gaacatgggg ccagagttct tgtcggcgtt taccgtaggc gaccagttgt tatggggcgc   1380
cgccgagccg ctgcgtcgaa tgctgcgcca gttggcgtag tggctattgc agcgcttatc   1440
gggcctgcgt gtggttctgt aggccggata aggcgcgtca gcgccgccat ccggcgggga   1500
aatttgtgtt aaaccagggg tgcatcgtca cccttttttt gcgtaataca ggagtaaacg   1560
cagatgtttc attttatca ggagttaagc agagcattgg ctattcttta agggtagctt   1620
aatcccacgg gtattaagcc taacctgaag gtaggacgac gcagatagga tgcacagtgt   1680
gctgcgccgt tcaggtcaaa gaagtgtcac tacctgatgt tgaattggaa gatcc        1735
```

<210> SEQ ID NO 2
<211> LENGTH: 391
<212> TYPE: PRT
<213> ORGANISM: Salmonella typhimurium

<400> SEQUENCE: 2

```
Met Val Lys Asp Ala Pro Gln Asp Thr Gly Ala His Thr Gln His Ile
  1               5                  10                  15

Ser Leu Gln Glu Lys Asn Ala Met Lys Asn Val Gly Phe Ile Gly Trp
             20                  25                  30

Arg Gly Met Val Gly Ser Val Leu Met Gln Arg Met Val Glu Glu Arg
         35                  40                  45

Asp Phe Asp Ala Ile Arg Pro Val Phe Phe Ser Thr Ser Gln Phe Gly
     50                  55                  60

Gln Ala Ala Pro Thr Phe Gly Asp Thr Ser Thr Gly Thr Leu Gln Asp
 65                  70                  75                  80

Ala Phe Asp Leu Asp Ala Leu Lys Ala Leu Asp Ile Ile Val Thr Cys
                 85                  90                  95

Gln Gly Gly Asp Tyr Thr Asn Glu Ile Tyr Pro Lys Leu Arg Glu Ser
            100                 105                 110

Gly Trp Gln Gly Tyr Trp Ile Asp Ala Ala Ser Thr Leu Arg Met Lys
        115                 120                 125

Asp Asp Ala Ile Ile Ile Leu Asp Pro Val Asn Gln Asp Val Ile Thr
    130                 135                 140

Asp Gly Leu Asn Asn Gly Val Lys Thr Phe Val Gly Gly Asn Cys Thr
145                 150                 155                 160

Val Ser Leu Met Leu Met Ser Leu Gly Gly Leu Phe Ala His Asn Leu
                165                 170                 175

Val Asp Trp Val Ser Val Ala Thr Tyr Gln Ala Ala Ser Gly Gly Gly
            180                 185                 190

Ala Arg His Met Arg Glu Leu Leu Thr Gln Met Gly Gln Leu Tyr Gly
        195                 200                 205

His Val Ala Asp Glu Leu Ala Thr Pro Ser Ser Ala Ile Leu Asp Ile
    210                 215                 220
```

```
Glu Arg Lys Val Thr Ala Leu Thr Arg Ser Gly Glu Leu Pro Val Asp
225                 230                 235                 240

Asn Phe Gly Val Pro Leu Ala Gly Ser Leu Ile Pro Trp Ile Asp Lys
                245                 250                 255

Gln Leu Asp Asn Gly Gln Ser Arg Glu Glu Trp Lys Gly Gln Ala Glu
            260                 265                 270

Thr Asn Lys Ile Leu Asn Thr Ala Ser Val Ile Pro Val Asp Gly Leu
        275                 280                 285

Cys Val Arg Val Gly Ala Leu Arg Cys His Ser Gln Ala Phe Thr Ile
    290                 295                 300

Lys Leu Lys Lys Glu Val Ser Ile Pro Thr Val Glu Glu Leu Leu Ala
305                 310                 315                 320

Ala His Asn Pro Trp Ala Lys Val Val Pro Asn Asp Arg Asp Ile Thr
                325                 330                 335

Met Arg Glu Leu Thr Pro Ala Ala Val Thr Gly Thr Leu Thr Thr Pro
            340                 345                 350

Val Gly Arg Leu Arg Lys Leu Asn Met Gly Pro Glu Phe Leu Ser Ala
        355                 360                 365

Phe Thr Val Gly Asp Gln Leu Leu Trp Gly Ala Ala Glu Pro Leu Arg
    370                 375                 380

Arg Met Leu Arg Gln Leu Ala
385                 390

<210> SEQ ID NO 3
<211> LENGTH: 1961
<212> TYPE: DNA
<213> ORGANISM: Salmonella typhimurium and Pseudomonas putida

<400> SEQUENCE: 3
ggatcttccc taaatttaaa tataaacaac gaattatctc cttaacgtac gttttcgttc      60
cattggccct caaaccccta attaggatca ataaaacagc gacggaaatg attcccttcc    120
taacgcaaat tccctgataa tcgccactgg actttctgct tgcgcggtaa ggcaggataa    180
gtcgcattac tgatggcttc gctatcattg attaatttca cttgcgactt tggctgcttt    240
ttgtatggtg aaggatgcgc acaggatac tggcgcgcat acacagcaca tctctttgca     300
ggaaaaaaac gctatgaaaa atgttggttt tatcggctgg cgcggaatgg tcggctctgt    360
tctcatgcaa cgcatggtag aggagcgcga tttcgacgct attcgccctg ttttcttttc    420
tacctcccag tttggacagg cggcgcccac cttcggcgac acctccaccg gcacgctaca    480
ggacgctttt gatctggatg cgctaaaagc gctcgatgat ctatgaagag gtgacgtcat    540
gaacaaaggt gtaatgcgac cgggccatgt gcagctgcgt gtactggaca tgagcaaggc    600
cctggaacac tacgtcgagt tgctgggcct gatcgagatg gaccgtgacg accagggccg    660
tgtctatctg aaggcttgga ccgaagtgga taagttttcc ctggtgctac gcaggctga    720
cgagccgggc atggatttta tgggtttcaa ggttgtggat gaggatgctc tccggcaact    780
ggagcgggat ctgatggcat atggctgtgc cgttgagcag ctaccccgcag gtgaactgaa    840
cagttgtggc cggcgcgtgc gttccaggcc ctccgggcat cacttcgagt tgtatgcaga    900
caaggaatat actggaaagt ggggtttgaa tgacgtcaat cccgaggcat ggccgcgcga    960
tctgaaaggt atggcggctg tgcgtttcga ccacgccctc atgtatggcg acgaattgcc   1020
ggcgacctat gacctgttca ccaaggtgct cggtttctat ctggccgaac aggtgctgga   1080
cgaaaatggc acgcgcgtcg cccagtttct cagtctgtcg accaaggccc acgacgtggc   1140
```

```
cttcattcac catccggaaa aaggccgcct ccatcatgtg tccttccacc tcgaaacctg    1200
ggaagacttg cttcgcgccg ccgacctgat ctccatgacc gacacatcta tcgatatcgg    1260
cccaacccgc cacggcctca ctcacggcaa gaccatctac ttcttcgacc cgtccggtaa    1320
ccgcaacgaa gtgttctgcg ggggagatta caactacccg gaccacaaac cggtgacctg    1380
gaccaccgac cagctgggca aagccttctt ttaccacgac cgcattctca acgaacgatt    1440
catgaccgtg ctgacctgat ggtccggaga tcatcactat cgcgaatta accccggcgg    1500 cggtgaccgg cacgttgact acgccggttg gtcgtctgcg taagctgaac atggggccag    1560
agttcttgtc ggcgtttacc gtaggcgacc agttgttatg gggcgccgcc gagccgctgc    1620
gtcgaatgct cgccagttg gcgtagtggc tattgcagcg cttatcgggc ctgcgtgtgg    1680
ttctgtaggc cggataaggc gcgtcagcgc cgccatccgg cggggaaatt tgtgttaaac    1740 cagggggtgca tcgtcaccct tttttttgcgt aatacaggag taaacgcaga tgtttcatt    1800 ttatcaggag ttaagcagag cattggctat tctttaaggg tagcttaatc ccacgggtat    1860
taagcctaac ctgaaggtag gacgacgcag ataggatgca cagtgtgctg cgccgttcag    1920
gtcaaagaag tgtcactacc tgatgttgaa ttggaagatc c                        1961
```

<210> SEQ ID NO 4
<211> LENGTH: 454
<212> TYPE: PRT
<213> ORGANISM: Salmonella typhimurium and Pseudomonas putida

<400> SEQUENCE: 4

```
Met Val Lys Asp Ala Pro Gln Asp Thr Gly Ala His Thr Gln His Ile
  1               5                  10                  15

Ser Leu Gln Glu Lys Asn Ala Met Lys Asn Val Gly Phe Ile Gly Trp
             20                  25                  30

Arg Gly Met Val Gly Ser Val Leu Met Gln Arg Met Val Glu Glu Arg
         35                  40                  45

Asp Phe Asp Ala Ile Arg Pro Val Phe Phe Ser Thr Ser Gln Phe Gly
     50                  55                  60

Gln Ala Ala Pro Thr Phe Gly Asp Thr Ser Thr Gly Thr Leu Gln Asp
 65                  70                  75                  80

Ala Phe Asp Leu Asp Ala Leu Lys Ala Leu Asp Met Asn Lys Gly Val
                 85                  90                  95

Met Arg Pro Gly His Val Gln Leu Arg Val Leu Asp Met Ser Lys Ala
            100                 105                 110

Leu Glu His Tyr Val Glu Leu Leu Gly Leu Ile Glu Met Asp Arg Asp
        115                 120                 125

Asp Gln Gly Arg Val Tyr Leu Lys Ala Trp Thr Glu Val Asp Lys Phe
    130                 135                 140

Ser Leu Val Leu Arg Glu Ala Asp Glu Pro Gly Met Asp Phe Met Gly
145                 150                 155                 160

Phe Lys Val Val Asp Glu Asp Ala Leu Arg Gln Leu Glu Arg Asp Leu
                165                 170                 175

Met Ala Tyr Gly Cys Ala Val Glu Gln Leu Pro Ala Gly Glu Leu Asn
            180                 185                 190

Ser Cys Gly Arg Arg Val Arg Ser Arg Pro Ser Gly His His Phe Glu
        195                 200                 205

Leu Tyr Ala Asp Lys Glu Tyr Thr Gly Lys Trp Gly Leu Asn Asp Val
    210                 215                 220

Asn Pro Glu Ala Trp Pro Arg Asp Leu Lys Gly Met Ala Ala Val Arg
```

```
                    225                 230                 235                 240

Phe Asp His Ala Leu Met Tyr Gly Asp Glu Leu Pro Ala Thr Tyr Asp
                        245                 250                 255

Leu Phe Thr Lys Val Leu Gly Phe Tyr Leu Ala Glu Gln Val Leu Asp
                        260                 265                 270

Glu Asn Gly Thr Arg Val Ala Gln Phe Leu Ser Leu Ser Thr Lys Ala
                        275                 280                 285

His Asp Val Ala Phe Ile His His Pro Glu Lys Gly Arg Leu His His
                        290                 295                 300

Val Ser Phe His Leu Glu Thr Trp Glu Asp Leu Leu Arg Ala Ala Asp
        305                 310                 315                 320

Leu Ile Ser Met Thr Asp Thr Ser Ile Asp Ile Gly Pro Thr Arg His
                        325                 330                 335

Gly Leu Thr His Gly Lys Thr Ile Tyr Phe Phe Asp Pro Ser Gly Asn
                        340                 345                 350

Arg Asn Glu Val Phe Cys Gly Gly Asp Tyr Asn Tyr Pro Asp His Lys
                        355                 360                 365

Pro Val Thr Trp Thr Thr Asp Gln Leu Gly Lys Ala Phe Phe Tyr His
                        370                 375                 380

Asp Arg Ile Leu Asn Glu Arg Phe Met Thr Val Leu Thr Ile Thr Met
        385                 390                 395                 400

Arg Glu Leu Thr Pro Ala Ala Val Thr Gly Thr Leu Thr Thr Pro Val
                        405                 410                 415

Gly Arg Leu Arg Lys Leu Asn Met Gly Pro Glu Phe Leu Ser Ala Phe
                        420                 425                 430

Thr Val Gly Asp Gln Leu Leu Trp Gly Ala Ala Glu Pro Leu Arg Arg
                        435                 440                 445

Met Leu Arg Gln Leu Ala
                        450

<210> SEQ ID NO 5
<211> LENGTH: 91
<212> TYPE: PRT
<213> ORGANISM: Salmonella typhimurium

<400> SEQUENCE: 5

Met Val Lys Asp Ala Pro Gln Asp Thr Gly Ala His Thr Gln His Ile
        1               5                   10                  15

Ser Leu Gln Glu Lys Asn Ala Met Lys Asn Val Gly Phe Ile Gly Trp
                        20                  25                  30

Arg Gly Met Val Gly Ser Val Leu Met Gln Arg Met Val Glu Glu Arg
                        35                  40                  45

Asp Phe Asp Ala Ile Arg Pro Val Phe Phe Ser Thr Ser Gln Phe Gly
                        50                  55                  60

Gln Ala Ala Pro Thr Phe Gly Asp Thr Ser Thr Gly Thr Leu Gln Asp
        65                  70                  75                  80

Ala Phe Asp Leu Asp Ala Leu Lys Ala Leu Asp
                        85                  90

<210> SEQ ID NO 6
<211> LENGTH: 306
<212> TYPE: PRT
<213> ORGANISM: Pseudomonas putida

<400> SEQUENCE: 6

Met Asn Lys Gly Val Met Arg Pro Gly His Val Gln Leu Arg Val Leu
```

```
                1               5               10              15
Asp Met Ser Lys Ala Leu Glu His Tyr Val Glu Leu Leu Gly Leu Ile
                20                      25                      30

Glu Met Asp Arg Asp Asp Gln Gly Arg Val Tyr Leu Lys Ala Trp Thr
                35                      40                      45

Glu Val Asp Lys Phe Ser Leu Val Leu Arg Glu Ala Asp Glu Pro Gly
                50                      55                      60

Met Asp Phe Met Gly Phe Lys Val Val Asp Glu Asp Ala Leu Arg Gln
65                      70                      75                      80

Leu Glu Arg Asp Leu Met Ala Tyr Gly Cys Ala Val Glu Gln Leu Pro
                85                      90                      95

Ala Gly Glu Leu Asn Ser Cys Gly Arg Arg Val Arg Ser Arg Pro Ser
                100                     105                     110

Gly His His Phe Glu Leu Tyr Ala Asp Lys Glu Tyr Thr Gly Lys Trp
                115                     120                     125

Gly Leu Asn Asp Val Asn Pro Glu Ala Trp Pro Arg Asp Leu Lys Gly
130                     135                     140

Met Ala Ala Val Arg Phe Asp His Ala Leu Met Tyr Gly Asp Glu Leu
145                     150                     155                     160

Pro Ala Thr Tyr Asp Leu Phe Thr Lys Val Leu Gly Phe Tyr Leu Ala
                165                     170                     175

Glu Gln Val Leu Asp Glu Asn Gly Thr Arg Val Ala Gln Phe Leu Ser
                180                     185                     190

Leu Ser Thr Lys Ala His Asp Val Ala Phe Ile His His Pro Glu Lys
                195                     200                     205

Gly Arg Leu His His Val Ser Phe His Leu Glu Thr Trp Glu Asp Leu
210                     215                     220

Leu Arg Ala Ala Asp Leu Ile Ser Met Thr Asp Thr Ser Ile Asp Ile
225                     230                     235                     240

Gly Pro Thr Arg His Gly Leu Thr His Gly Lys Thr Ile Tyr Phe Phe
                245                     250                     255

Asp Pro Ser Gly Asn Arg Asn Glu Val Phe Cys Gly Gly Asp Tyr Asn
                260                     265                     270

Tyr Pro Asp His Lys Pro Val Thr Trp Thr Thr Asp Gln Leu Gly Lys
                275                     280                     285

Ala Phe Phe Tyr His Asp Arg Ile Leu Asn Glu Arg Phe Met Thr Val
                290                     295                     300

Leu Thr
305
```

<210> SEQ ID NO 7
<211> LENGTH: 315
<212> TYPE: DNA
<213> ORGANISM: Salmonella typhimurium

<400> SEQUENCE: 7

```
tggctattgc agcgcttatc gggcctgcgt gtggttctgt aggccggata aggcgcgtca    60
gcgccgccat ccggcgggga aatttgtgtt aaaccagggg tgcatcgtca ccctttttt    120
gcgtaataca ggagtaaacg cagatgtttc attttatca ggagttaagc agagcattgg     180
ctattcttta agggtagctt aatcccacgg gtattaagcc taacctgaag gtaggacgac    240
gcagatagga tgcacagtgt gctgcgccgt tcaggtcaaa gaagtgtcac tacctgatgt    300
tgaattggaa gatcc                                                     315
```

```
<210> SEQ ID NO 8
<211> LENGTH: 144
<212> TYPE: DNA
<213> ORGANISM: Escherichia coli

<400> SEQUENCE: 8
attctgaaat gagctgttga caattaatca tccggtcgta taatgtgtgg aattgtgagc      60
ggataacaat ttcacacagg aaacagacca tgggaattcg caattcccgg ggatccgtcg     120
acctgcagcc aagctcccaa gctt                                            144
```